US007381572B2

(12) United States Patent
Ebright et al.

(10) Patent No.: US 7,381,572 B2
(45) Date of Patent: *Jun. 3, 2008

(54) REAGENTS AND PROCEDURES FOR MULTI-LABEL HIGH-SPECIFICITY LABELING

(75) Inventors: Richard H. Ebright, North Brunswick, NJ (US); Yon W. Ebright, North Brunswick, NJ (US)

(73) Assignee: Rutgers, The State University of New Jersey, New Brunswick, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/256,900

(22) Filed: Oct. 24, 2005

(65) Prior Publication Data
US 2006/0141530 A1    Jun. 29, 2006

Related U.S. Application Data

(60) Provisional application No. 60/638,440, filed on Dec. 23, 2004.

(51) Int. Cl.
*G01N 33/533* (2006.01)
*G01N 21/76* (2006.01)
*G01N 21/00* (2006.01)
*G01N 33/53* (2006.01)
*C07K 1/13* (2006.01)
*C07D 209/04* (2006.01)

(52) U.S. Cl. ...................... 436/546; 436/544; 436/172; 436/164; 436/800; 436/805; 435/7.1; 435/968; 435/69.7; 530/402; 530/408; 548/102; 548/402

(58) Field of Classification Search ................ 436/544, 436/546, 172, 164, 800, 805; 435/7.1, 968, 435/69.7; 530/402, 408; 548/102, 402
See application file for complete search history.

(56) References Cited

U.S. PATENT DOCUMENTS 4,981,977 A    1/1991    Southwick et al.
(Continued)

FOREIGN PATENT DOCUMENTS

EP    0 747 448 A2    11/1996
(Continued)

OTHER PUBLICATIONS

Birch, Martyn et al., 'Dark 'Cyanine Dyes §: Their Synthesis And Use As Quenching Partners In Fluorescence Based Assays, Amersham Pharmacia Biotech, The Fourth International Symposium on Functional Dyes, May 31-Jun. 4, 1999, Osaka, Japan, 1 page.
(Continued)

*Primary Examiner*—Long V. Le
*Assistant Examiner*—Shafiqul Haq
(74) *Attorney, Agent, or Firm*—Hoffmann & Baron, LLP

(57) ABSTRACT

A detectable complex and methods for use thereof are provided herein. The detectable complex includes: at least one target material; a first peptide tag bound to the at least one target material; and a second peptide tag bound to the at least one target material. The complex further includes a first conjugate having a detectable group and two pendant phenylarsine moieties comprising a first tag binding group; wherein the first conjugate preferentially associates with the first peptide tag; and a second conjugate having a detectable group and two pendant phenylarsine moieties comprising a second tag binding group; wherein the second conjugate preferentially associates with the second peptide tag. The mean distance and/or mean angle between the pendant phenylarsine moieties in the first conjugate is different from the mean distance and/or mean angle between the pendant phenylarsine moieties in the second conjugate. Further provided herein are useful peptide tag combinations, target materials or sets of target materials including these peptide tag combinations, and nucleic acids or nucleic acid sets encoding these compositions.

21 Claims, 9 Drawing Sheets

U.S. PATENT DOCUMENTS

| | | | |
|---|---|---|---|
| 5,627,027 | A | 5/1997 | Waggoner |
| 5,932,474 | A | 8/1999 | Tsien et al. |
| 6,008,378 | A | 12/1999 | Tsien et al. |
| 6,054,271 | A | 4/2000 | Tsien et al. |
| 6,086,737 | A | 7/2000 | Patonay et al. |
| 6,130,094 | A | 10/2000 | Waggoner et al. |
| 6,133,445 | A | 10/2000 | Waggoner et al. |
| 6,197,928 | B1 | 3/2001 | Tsien et al. |
| 6,225,050 | B1 | 5/2001 | Waggoner |
| 6,451,569 | B1 | 9/2002 | Tsien et al. |
| 2005/0130167 | A1* | 6/2005 | Bao et al. ............ 435/6 |

FOREIGN PATENT DOCUMENTS

| | | |
|---|---|---|
| EP | 0 747 700 A2 | 11/1996 |
| EP | 0 747 700 B1 | 5/2001 |
| WO | WO 99/31181 | 6/1999 |
| WO | WO 03/091689 A2 | 11/2003 |
| WO | WO 03/091689 A3 | 11/2003 |

OTHER PUBLICATIONS

Clegg, Robert M., "Fluorescence Resonance Energy Transfer and Nucleic Acids", Methods in Enzymology, vol. 211, 1992, pp. 353-388.

Kapanidis et al., "Mean DNA Bend Angle and Distribution of DNA Bend Angles in the CAP-DNA Complex in Solution", Journal of Molecular Biology, (2001) 312, pp. 453-468.

Park, H. et al., "Nanometre localization of single ReAsH molecules", Journal of Microscopy, vol. 216, Pt 3 Dec. 2004, pp. 199-205.

Adams, et al., "New Biarsenical Ligands and Tetracysteine Motifs for Protein Labeling in Vitro and in Vivo: Synthesis and Biological Applications", Journal of American Chemical Society, 2002, vol. 124, No. 21, pp. 6063-6076.

Stroffekova et al., "The protein-labeling reagent FLASH-EDT$_2$ binds not only to CCXXCC motifs but also non-specifically to endogenous cysteine-rich proteins", Pflügers Arch—Eur J. Physiol (2001) 442: pp. 859-866.

Mujumdar et al., "Cyanine Dye Labeling Reagents: Sulfoindolcyanine Succinimidyl Esters", Bioconjuage Chemistry, Mar./Apr. 1993, vol. 4, No. 2, pp. 106-111.

Nakanishi et al., "Imaging of Conformational Changes of Proteins with a New Environment-Sensitive Fluorescent Probe Designed for Site-Specific Labeling of Recombinant Proteins in Live Cells", Analytical Chemistry, vol. 73, No. 13, Jul. 1, 2001, pp. 2920-2928.

Kapanidis et al., Site-Specific incorporation of Fluorescent Probes into Protein: Hexahistidine-Tag-Mediated Fluorescent Labeling with $(Ni^{2+}:$ Nitrilotriacetic Acid$)_n$ Fluorochrome Conjugates, Journal of American Chemical Society 2001, 123, pp. 12123-12125.

Griffin et al., "Specific Covalent Labeling of Recombinant Protein Molecules Inside Live Cells", Science, Jul. 10, 1998, vol. 281, No. 5374, pp. 269-272.

Wu et al., "Resonance Energy Transfer: Methods and Applications", Analytical Biochemistry—Methods in the Biological Sciences, vol. 218, No. 1, Apr. 1994, pp. 1-13.

Chen et al., "Fluorescence Polarization: Measurement with Ultraviolet-Polarizing Filters in a Spectrophotofluorometer", Science, Feb. 12, 1965, vol. 147, pp. 729-732.

* cited by examiner

REAGENTS AND PROCEDURES FOR MULTI-LABEL HIGH-SPECIFICITY LABELING

CROSS-REFERENCE TO RELATED APPLICATIONS

The present application claims the benefit of U.S. Provisional Application Ser. No. 60/638,440, filed Dec. 23, 2004, which is incorporated herein by reference.

This invention was made with Government support under Grant No. NIH R01-GM41376, awarded by the National Institutes of Health. Therefore, the Government has certain rights in this invention.

FIELD OF THE INVENTION

The present invention relates to detectable complexes including at least one target molecule of interest and multiple fluorescent bis-phenylarsine labels. The labels bind to one or a set of target molecules in a multi-site-specific fashion.

BACKGROUND OF THE INVENTION

Characterization of proteins often requires the ability to incorporate detectable groups—e.g., fluorochromes, chromophores, spin labels, radioisotopes, paramagnetic atoms, heavy atoms, haptens, crosslinking agents, and cleavage agents—at specific, defined sites. For proteins that do not contain pre-existing cysteine residues, site-specific labeling can be accomplished by use of site-directed mutagenesis to introduce a cysteine residue at the site of interest, followed by cysteine-specific chemical modification to incorporate the labeled probe. However, for proteins that contain pre-existing cysteine residues, site-specific labeling is difficult. Multiple strategies have been reported: (i) intein-mediated labeling ("expressed protein ligation"), (Muir, et al., *Proc. Natl. Acad. Sci. USA*, 95:6705-6710 (1998)); (ii) trans-glutaminase-mediated labeling (Sato et al., *Biochem.* 35:13072-13080 (1996)); (iii) oxidation-mediated labeling (Geoghegan, et al., *Bioconj. Chem.*, 3:138-146 (1992)); (iv) transition-metal-chelate-mediated labeling (Kapanidis et al., *J. Amer. Chem. Soc.*, 123:12123 (2001)); and (v) trivalent-arsenic-mediated labeling (see, for example, Griffin et al., *Science* 281:269-272, 1998; U.S. Pat. Nos. 6,008,378 and 6,451,569 B1 to Tsien et al.; and copending, commonly owned U.S. application Ser. No. 10/461,224). Strategies (i)-(iii) do not permit in situ labeling (i.e., direct labeling of proteins in cuvettes, gels, blots, or biological samples—without the need for a subsequent purification step) or in vivo labeling (i.e., direct labeling of proteins in living cells). Strategy (iv) does not permit labeling and analysis at sub-nanomolar concentrations. Strategy (v) is the most useful in that it permits both in situ and in vivo labeling. However, strategy (v) previously has been limited to site-specific labeling with single fluorescent probes, and "statistical" labeling with multiple fluorescent probes. For example, in the "statistical" multi-labeling approach, probes A and B are reacted simultaneouslly with a target molecule or set of target molecules having two peptide tags, A' and B', and three possible products are formed: A:A'/A:B', B:A'/B:B' and A:A'/B:B'. However, only product A:A'/B:B' has the desired properties. It would be preferred to provide a labeling method wherein probe A specifically bound only to tag A', and wherein probe B specifically bound only to tag B', so as to yield a defined, labeled product having the most desirable properties.

There is a need for improved methods and compositions for protein labeling that permit in situ labeling, that permit in vivo labeling, that permit labeling and analysis at sub-nanomolar concentrations, and that encompass a wide range of detectable groups with different properties. There is also a need in the art to prepare defined mult-labeled products. In particular, there is a need to extend the strategy of using arsenic-mediated labeling to permit orthogonal molecule-specific, site-specific labeling of target molecules, such as proteins, with multiple labels.

SUMMARY OF THE INVENTION

The present invention provides a detectable complex including: at least one target material; a first peptide tag bound to the at least one target material; and a second peptide tag bound to the at least one target material. The detectable complex of the present invention also includes at least two different labels referred to herein as a first conjugate and a second conjugate, which can bind in a multi-site-specific fashion to the at least one target material. The first conjugate has a detectable group and two pendant phenylarsine moieties comprising a first tag binding group; wherein the first conjugate preferentially associates with the first peptide tag. The second conjugate has a detectable group and two pendant phenylarsine moieties comprising a second tag binding group; wherein the second conjugate preferentially associates with the second peptide tag. The mean distance and/or mean angle between the pendant phenylarsine moieties in the first conjugate is different from the mean distance and/or mean angle between the pendant phenylarsine moieties in the second conjugate.

Preferably, at least one of the first and second conjugates having the two pendant phenylarsine moieties is a molecule according to the general structural Formula (I) and tautomers, acids, and salts thereof:

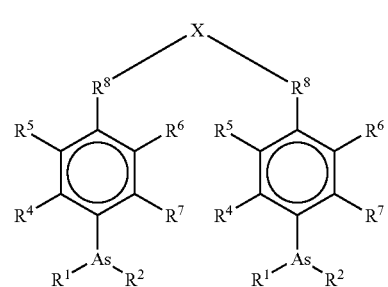

(I)

wherein:
(i) each $R^1$ or $R^2$, independently, is $O^-$, $S^-$, $OR^3$ or $SR^3$ with the provision that if either $R^1$ or $R^2$ is absent, the other remaining group is $=O$ or $=S$; or $R^1$ and $R^2$, together with the arsenic atom, form a ring according to one of the general structural Formulae (II), (III), (IV), or (V):

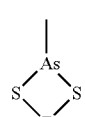

(II)

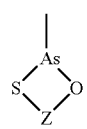

(III)

-continued

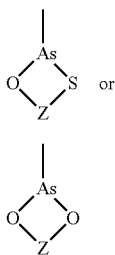

wherein $R^3$ is H, CH(OH)CH$_2$OH, or (CH$_2$)$_q$—Y, wherein q is 1-4 and Y is H, OH, NH$_2$, SH, COOH, OAc, CONH$_2$ or CN; and Z represents a saturated or unsaturated hydrocarbon chain comprising 2-4 singly or doubly bonded carbon atoms wherein each carbon atom may be further substituted with one or more groups selected from hydrogen, methyl, ethyl, 1-propyl, 2-propyl, methoxy, hydroxy, amino, carboxy, sulfo, oxo, thio, halo (fluoro, chloro, bromo, or fluoro) and (CH$_2$)$_{n''}$SO$_3$, wherein n" is 1 or 2;

(ii) $R^4$, $R^5$, $R^6$ and $R^7$ are each independently H, F, OR$^3$, R$^3$, OAc, NH$_2$, N(C$_1$-C$_4$ alkyl)$_2$, R$^1$; or R$^4$ together with R$^5$, or R$^6$ together with R$^7$, or both, form a ring;

(iii) $R^8$ is a linear or branched spacer having a minimum length (when fully extended) of about 1.5, preferably 2.5, more preferably 3.5, and most preferably 4.5 Ångstroms and having a maximum length (when fully extended) of about 15, preferably 12.5, more preferably 10, and most preferably 7.5 Ångstroms; and (v) X is a detectable group.

A particularly preferred molecule according to Formula (I) for use in the compositions and methods of the present invention is one wherein $R^1$ and $R^2$, together with the arsenic atom, form a ring according to one of the general Formulae (II), (III), (IV), or (V) when Z is CH$_2$SO$_3$.

As will be described in further detail below, X in Formula (1) is desirably a fluorescent moiety, such as a cyanine or squaraine derivative, which can be selected such that the mean distance and/or mean angle between the pendant phenylarsine moieties in at least one of the conjugates is distinct from the mean distance and/or mean angle between the pendant phenylarsine moieties in the other of the conjugates.

The detectable complex of the present invention can also include, as one of the first or second conjugates, a molecule represented by the general structural Formula (II) and tautomers, anhydrides and salts thereof:

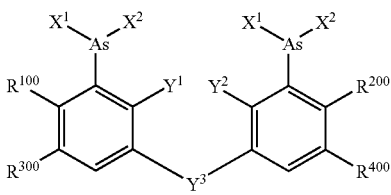

(II)

wherein each $X^1$ or $X^2$, independently is Cl, Br, I, OR$^a$, or SR$^a$, or $X^1$ and $X^2$ together with the arsenic atom form a ring having the structure:

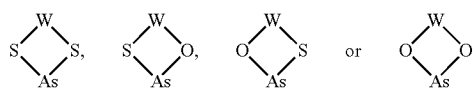

$R^a$ is H, C$_1$-C$_4$ alkyl, CH$_2$CH$_2$OH, CH$_2$COOH, or CN;

W is 1,2-ethanediyl, 1,2-propanediyl, 2,3-butanediyl, 1,3-propanediyl, 1,2-benzenediyl, 4-methyl-1,2-benzenediyl, 1,2-cyclopentanediyl, 1,2-cyclohexanediyl, 3-hydroxy-1,2-propanediyl, 3-sulfo-1,2-propanediyl, or 1,2-bis (carboxy)-1,2-ethanediyl;

$Y^1$ and $Y^2$, independently, are H or CH$_3$; or $Y^1$ and $Y^2$, together form a ring such that the biarsenical molecule has the general structure formula:

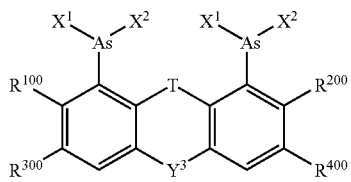

wherein T is O, S, CH$_2$, C(CH$_3$)$_2$, or NH;

$R^{100}$ and $R^{200}$, independently, are OR$^a$, OAc, NR$^a$R$^b$, or H;

$R^{300}$ and $R^{400}$, independently, are H, F, Cl, Br, I, OR$^a$, or R$^a$; or $R^{100}$ together with $R^{300}$, or $R^{200}$ together with $R^{400}$, or both, form a ring in which (i) one of $R^{100}$ or $R^{300}$ is C$_2$-C$_3$ alkyl and the other is NR$^a$ and (ii) one of $R^{200}$ and $R^{400}$ is C$_2$-C$_3$ alkyl and the other is NR$^a$;

$R^b$ is H, C$_1$-C$_4$ alkyl, CH$_2$CH$_2$OH, CH$_2$COOH, or CN;

$Y^3$ is CR$^a$R$^b$, Cr$^a$OR$^b$, C=O, or a spirolactone having one of the structures:

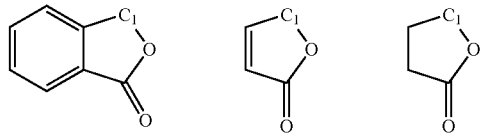

wherein the spiro linkage is formed at $C_1$.

In the detectable complex of the present invention, one or more positions of Formula II is substituted so as to add a detectable group. Desirably, the detectable group at one or more positions of Formula (II) is a fluorescent moiety selected from fluorescein, resorufin and derivatives thereof.

With reference to FIG. 2, the present invention further provides methods for labeling and/or detecting at least one target material. In one embodiment, the method includes the step of providing the following: at least one target material; a first peptide tag bound to the at least one target material; and a second peptide tag bound to the at least one target material. The method further includes reacting the at least one target material with the following under suitable conditions to allow labeling of the target material: (i) a first conjugate having a detectable group and two pendant phenylarsine moieties comprising a first tag binding group; wherein the first conjugate preferentially associates with the first peptide tag; and (ii) a second conjugate having a detectable group and two pendant phenylarsine moieties comprising a second tag binding group; wherein the second conjugate preferentially associates with the second peptide tag. The mean distance and/or mean angle between the pendant phenylarsine moieties in the first conjugate is different from the mean distance and/or mean angle between the pendant phenylarsine moieties in the second conjugate. The method can also include the step of detecting the conjugates, thereby detecting the at least one target material.

FIG. 2 depicts multisite, multicolor fluorescence labeling technology. A. of FIG. 2 shows labeled target material that includes a protein, P, containing a first tetracysteine tag, $T_1$; a second, different tetracysteine tag $T_2$; a first biarsenical fluorochrome derivative, $F_1$, that binds to $T_1$; and a second, different biarsenical fluorochrome derivative, $F_2$, that binds to $T_2$. B. of FIG. 2 shows labeled target material that includes a first protein, $P_1$, containing a first tetracysteine tag, $T_1$, and a first biarsenical fluorochrome derivative, $F_1$, that binds to $T_1$; and a second protein, $P_2$, containing a second, different tetracysteine tag, $T_2$; and a second, different biarsenical fluorochrome derivative, $F_2$, that binds to $T_2$.

The invention further relates to a method for determining the localization, concentration or interactions of at least one target material of interest on or within a cell, tissue, organ or organism. The method includes the step of providing a cell, tissue, organ or organism containing: at least one target material; a first peptide tag bound to the at least one target material; and a second peptide tag bound to the at least one target material. The method also includes the step of contacting the cell, tissue, organ, or organism with the following components under suitable conditions to allow labeling of the at least one target material: (i) a first conjugate having a detectable group and two pendant phenylarsine moieties comprising a first tag binding group; wherein the first conjugate preferentially associates with the first peptide tag; and (ii) a second conjugate having a detectable group and two pendant phenylarsine moieties comprising a second tag binding group; wherein the second conjugate preferentially associates with the second peptide tag. The mean distance and/or mean angle between the pendant phenylarsine moieties in the first conjugate is different from the mean distance and/or mean angle between the pendant phenylarsine moieties in the second conjugate. The method also includes detecting the label, thereby determining the localization, concentration, or interactions of the target material.

Furthermore, provided herein is a method for monitoring a binding process. The method includes reacting a first component of a specific binding pair with a second component of the pair; the pair having bound thereto a first peptide tag and a second peptide tag and being labeled with the following: (i) a first conjugate having a detectable group and two pendant phenylarsine moieties comprising a first tag binding group; wherein the first conjugate preferentially associates with the first peptide tag; and (ii) a second conjugate having a detectable group and two pendant phenylarsine moieties comprising a second tag binding group; wherein the second conjugate preferentially associates with the second peptide tag. The method employs different labels (i.e., conjugates), wherein the mean distance and/or mean angle between the pendant phenylarsine moieties in the first conjugate is different from the mean distance and/or mean angle between the pendant phenylarsine moieties in the second conjugate. The method also includes the step of monitoring for a change in a property of a detectable group on at least one of the first and second conjugates in the presence of both components of the specific binding pair, as compared to in the presence of only one of the components of pair.

The present invention also provides an assay method for monitoring a reaction. The method includes reacting a first reactant of a reactant pair with a second reactant of said pair; the reactant pair having bound thereto a first peptide tag and a second peptide tag and being labeled with the following: (i) a first conjugate having a detectable group and two pendant phenylarsine moieties comprising a first tag binding group; wherein the first conjugate preferentially associates with the first peptide tag; and (ii) a second conjugate having a detectable group and two pendant phenylarsine moieties comprising a second tag binding group; wherein the second conjugate preferentially associates with the second peptide tag. The mean distance and/or mean angle between the pendant phenylarsine moieties in the first conjugate is different from the mean distance and/or mean angle between the pendant phenylarsine moieties in the second conjugate. The method further includes monitoring for a change in a property of a detectable group on at least one of the first and second conjugates in the presence of both of the reactants, as compared to in the presence of only one of the reactants.

Moreover, provided herein is a method for isolating at least one target material of interest. The method includes providing a solution including: at least one target material; a first peptide tag bound to the at least one target material; and a second peptide tag bound to the at least one target material. The method further includes the step of contacting the provided solution with first and second conjugates immobilized on a solid support under suitable conditions to allow binding of the at least one target material to the immobilized conjugates. The first conjugate has a detectable group and two pendant phenylarsine moieties comprising a first tag binding group; wherein the first conjugate preferentially associates with the first peptide tag. The second conjugate has a detectable group and two pendant phenylarsine moieties comprising a second tag binding group; wherein the second conjugate preferentially associates with the second peptide tag. The mean distance and/or mean angle between the pendant phenylarsine moieties in the first conjugate is different from the mean distance and/or mean angle between the pendant phenylarsine moieties in the second conjugate. The method also includes the step of eluting the target material with a low-molecular weight monothiol or low-molecular weight dithiol.

Furthermore, the present invention provides several kits. For example, the invention provides a kit that includes at least one vector including sequence encoding a first peptide tag and/or a second peptide tag. The first and second peptide tags can be encoded by sequence contained within a single vector. Alternatively, a first peptide tag can be encoded by sequence within a first vector, and a second peptide tag can be encoded by sequence within a second vector. This kit further includes a first conjugate having a detectable group and two pendant phenylarsine moieties comprising a first tag binding group; wherein the first conjugate preferentially associates with the first peptide tag. Also included within this kit of the present invention is a second conjugate having a detectable group and two pendant phenylarsine moieties comprising a second tag binding group; wherein the second conjugate preferentially associates with the second peptide tag. The labels (i.e., conjugates) in the kit are different in that the mean distance and/or mean angle between the pendant phenylarsine moieties in the first conjugate is different from the mean distance and/or mean angle between the pendant phenylarsine moieties in the second conjugate.

The invention also provides useful peptide tag combinations and target materials or target material sets including these tag combinations. Moreover, the invention provides isolated or recombinant nucleic acids or nucleic acid sets encoding these materials, which can be provided in kits.

For example, the present invention provides a composition including: (i) a peptide sequence of the form: $C(X)_iC(X)_jC(X)_kC$, wherein C is cysteine, X is any amino acid, and i, j, and k are each independently selected from 0 or an integer from 1-8; and (ii) a peptide sequence of the form $C(X)_iC$, wherein X is any amino acid and i is 0-6.

Further provided herein is a composition that includes: (i) at least one target material; (ii) a first peptide tag bound to the at least one target material and being of the form: $C(X)_iC(X)_jC(X)_kC$, wherein C is cysteine, X is any amino acid, and i, j, and k are each independently selected from 0 or an integer from 1-8; (iii) a second peptide tag bound to the at least one target material and being of the form $C(X)_iC$, wherein X is any amino acid and i is 0-6. The at least one target material can be a polypeptide or a set of polypeptides.

The invention also provides a composition including: (i) a first nucleic acid sequence encoding a first peptide tag of the form: $C(X)_iC(X)_jC(X)_kC$, wherein C is cysteine, X is any amino acid, and i, j, and k are each independently selected from 0 or an integer from 1-8; and (ii) a second nucleic acid sequence encoding a second peptide tag of the form $C(X)_iC$, wherein X is any amino acid and i is 0-6. This composition can be included within a kit according to the present invention. The first and second nucleic acid sequences can be provided on the same or different vectors within the kit, for example.

Moreover, the invention provides a composition including an isolated or recombinant nucleic acid or nucleic acid set encoding: (i) at least one target material; (ii) a first peptide tag bound to the at least one target material and being of the form: $C(X)_iC(X)_jC(X)_kC$, wherein C is cysteine, X is any amino acid, and i, j, and k are each independently selected from 0 or an integer from 1-8; and (iii) a second peptide tag bound to the at least one target material and being of the form $C(X)_iC$, wherein X is any amino acid and i is 0-6.95. The at least one target material can be a polypeptide or a set of polypeptides. Moreover, this composition can be provided in a kit according to the present invention. For example, a vector or set of vectors encoding components (i), (ii) and (iii) can be provided in kit form.

DETAILED DESCRIPTION OF THE INVENTION

Compositions of the Invention

Figure 1:
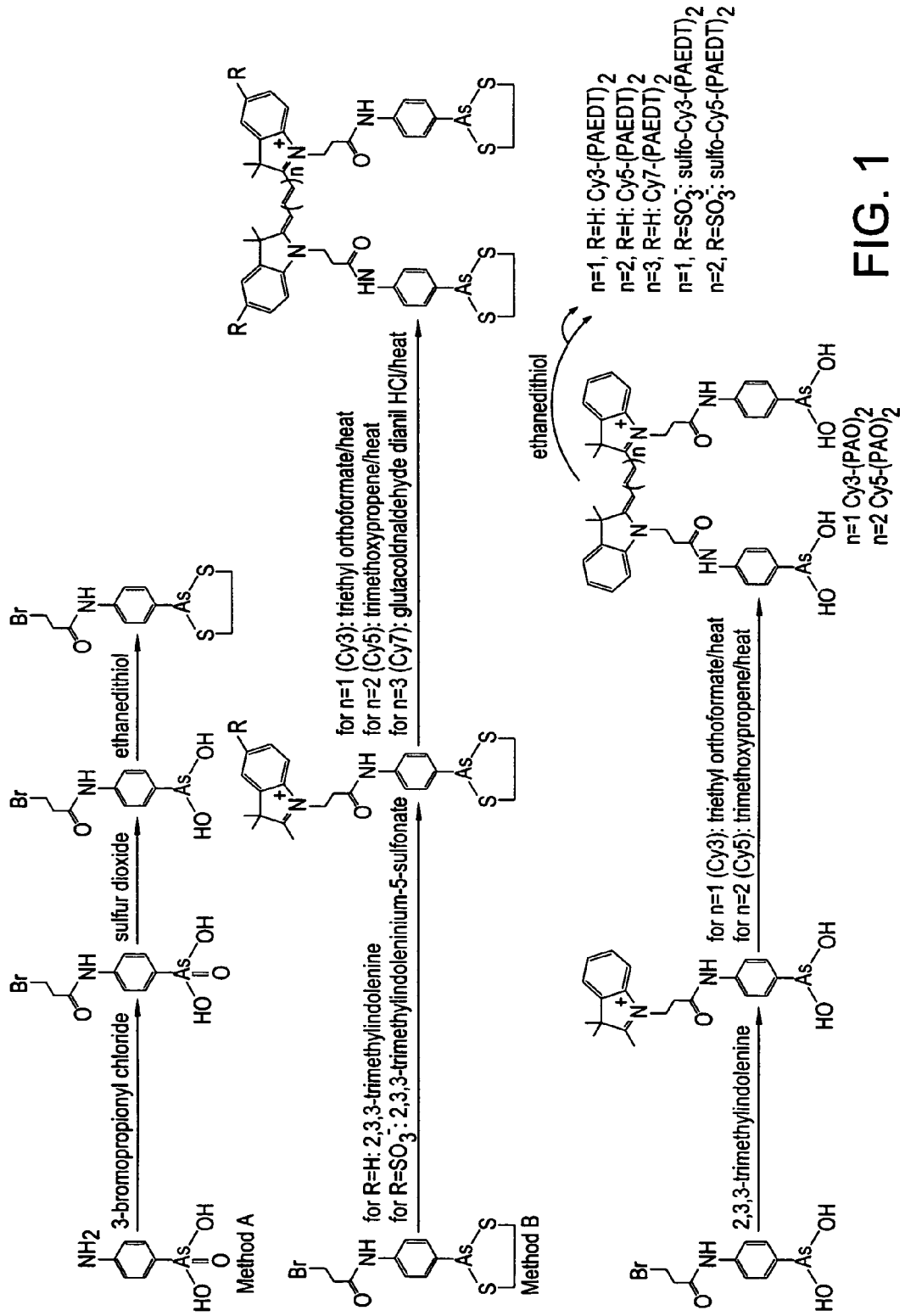
FIG. 1 depicts methods for synthesizing certain bis arsenical molecules employed in the compositions and methods of the invention.
Figure 2:
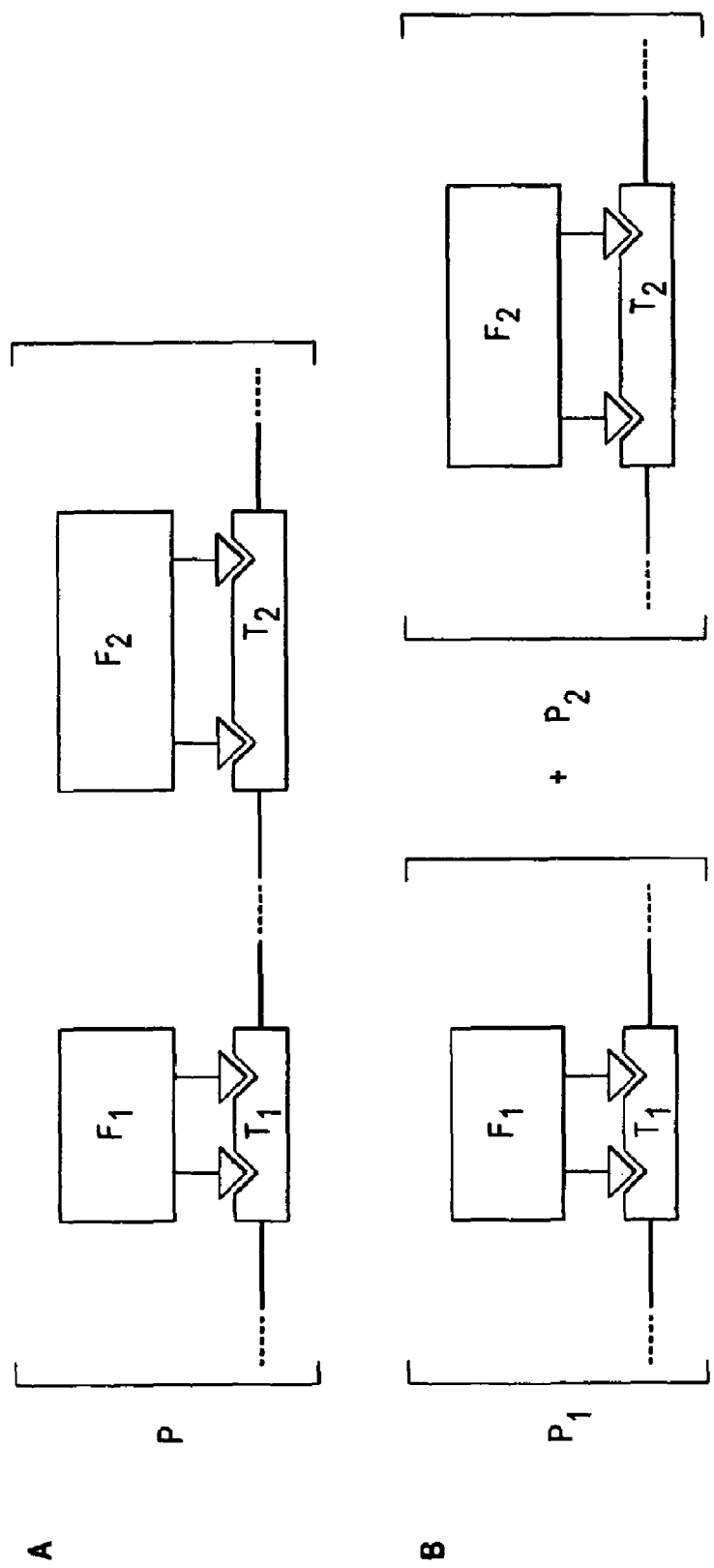
FIG. 2 depicts some embodiments of the fluorescence labeling technology of the present invention.

The invention provides detectable complexes including at least one target material labeled in a multi-site-specific fashion with multiple labels, which are referred to herein as conjugates. The conjugates each include a detectable group and two pendant phenylarsine moieties. Desirably, at least one of the conjugates in the detectable complex is a molecule with two pendant phenylarsine moieties according to the following general structural Formula (I) and tautomers, acids, and salts thereof:

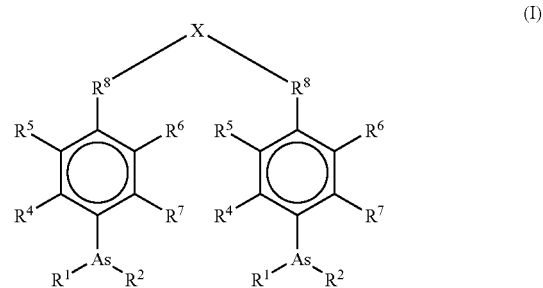

(I)

wherein:
(i) each $R^1$ or $R^2$, independently, is $O^-$, $S^-$, $OR^3$ or $SR^3$ with the provision that if either $R^1$ or $R^2$ is absent, the other remaining group is $=O$ or $=S$; or $R^1$ and $R^2$, together with the arsenic atom, form a ring according to one of the general structural Formulae (II), (III), (IV), or (V):

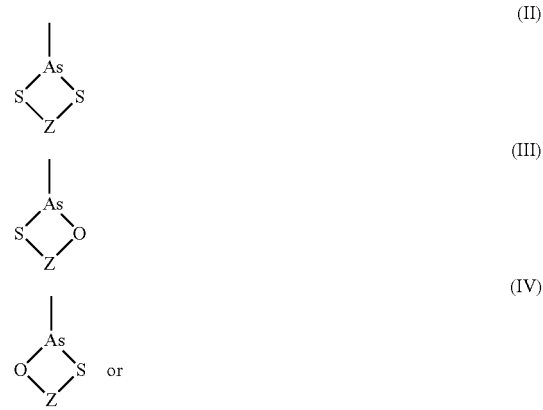

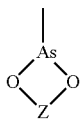
(V)

wherein R³ is H, CH(OH)CH₂OH, or (CH₂)$_q$—Y, wherein q is 14 and Y is H, OH, NH₂, SH, COOH, OAc, CONH₂ or CN; and Z represents a saturated or unsaturated hydrocarbon chain comprising 2-4 singly or doubly bonded carbon atoms wherein each carbon atom may be further substituted with one or more groups selected from hydrogen, methyl, ethyl, 1-propyl, 2-propyl, methoxy, hydroxy, amino, carboxy, sulfo, oxo, thio, halo (fluoro, chloro, bromo, or fluoro) and (CH₂)$_{n''}$SO₃, wherein n" is 1 or 2;

(ii) R⁴, R⁵, R⁶ and R⁷ are each independently H, F, OR³, R³, OAc, NH₂, N(C₁-C₄ alkyl)₂, R¹; or R⁴ together with R⁵, or R⁶ together with R⁷, or both, form a ring;

(iii) R⁸ is a linear or branched spacer having a minimum length (when fully extended) of about 1.5, preferably 2.5, more preferably 3.5, and most preferably 4.5 Ångstroms and having a maximum length (when fully extended) of about 15, preferably 12.5, more preferably 10, and most preferably 7.5 Ångstroms; and (v) X is a detectable group.

As described above, a particularly preferred molecule according to Formula (I) for use in the compositions and methods of the present invention is one wherein R¹ and R², together with the arsenic atom, form a ring according to one of the general Formulae (II), (III), (IV), or (V) when Z is CH₂SO₃.

In one embodiment, R⁸ comprises a chain having a minimum length of 1, preferably 2, and more preferably 3 non-hydrogen atoms and having a maximum length of 9, preferably 8, and more preferably 7 non-hydrogen atoms. Some examples of chains include —(CH₂)$_{1-7}$—C(O)NH— preferably —(CH₂)₂—C(O)NH—.

The detectable complex of the present invention can also include, as one of the first or second conjugates, a molecule represented by the general structural Formula (II) and tautomers, anhydrides and salts thereof:

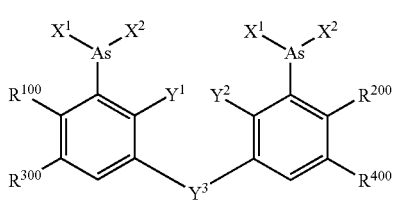
(II)

wherein each X¹ or X², independently is Cl, Br, I, OR$^a$, or SR$^a$, or X¹ and X² together with the arsenic atom form a ring having the structure:

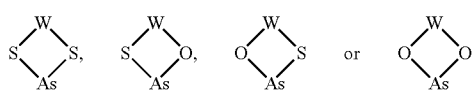

R$^a$ is H, C₁-C₄ alkyl, CH₂CH₂OH, CH₂COOH, or CN;

W is 1,2-ethanediyl, 1,2-propanediyl, 2,3-butanediyl, 1,3-propanediyl, 1,2-benzenediyl, 4-methyl-1,2-benzenediyl, 1,2-cyclopentanediyl, 1,2-cyclohexanediyl, 3-hydroxy-1, 2-propanediyl, 3-sulfo-1,2-propanediyl, or 1,2-bis (carboxy)-1,2-ethanediyl;

Y¹ and Y², independently, are H or CH₃; or

Y¹ and Y², together form a ring such that the biarsenical molecule has the general structure formula:

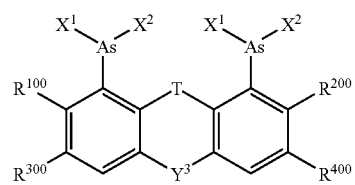

wherein T is O, S, CH₂, C(CH₃)₂, or NH;

R¹⁰⁰ and R²⁰⁰, independently, are OR$^a$, OAc, NR$^a$R$^b$, or H;

R³⁰⁰ and R⁴⁰⁰, independently, are H, F, Cl, Br, I, OR$^a$, or R$^a$; or

R¹⁰⁰ together with R³⁰⁰, or R²⁰⁰ together with R⁴⁰⁰, or both, form a ring in which
 (i) one of R¹⁰⁰ or R³⁰⁰ is C₂-C₃ alkyl and the other is NR$^a$ and
 (ii) one of R²⁰⁰ and R⁴⁰⁰ is C₂-C₃ alkyl and the other is NR$^a$;

R$^b$ is H, C₁-C₄ alkyl, CH₂CH₂OH, CH₂COOH, or CN;

Y³ is CR$^a$R$^b$, Cr$^a$OR$^b$, C=O, or a spirolactone having one of the structures:

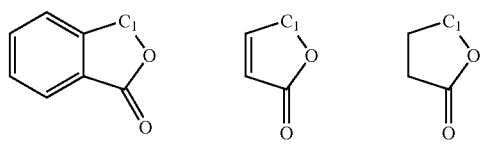

wherein the spiro linkage is formed at C₁.

When employed in a detectable complex according to the present invention, one or more positions of Formula II is substituted so as to add a detectable group. In some embodiments, the detectable group at one or more positions of Formula (II) is a fluorescent moiety selected from fluorescein, resorufin and derivatives thereof.

"Detectable group" as used herein refers to any chemical moiety that can be detected. Examples of detectable groups include fluorescent moieties, phosphorescent moieties, luminescent moieties, absorbent moieties, photosensitizers, spin labels, radioisotopes, isotopes detectable by nuclear magnetic resonance, paramagnetic atoms, heavy atoms, haptens, crosslinking agents, cleavage agents, and combinations thereof.

The detectable group on the first and/or second conjugates in the detectable complex of the present invention may be detected by monitoring a signal. Some signals which may be monitored due to the presence of a detectable group include, for example, fluorescence (fluorescence emission intensity, fluorescence lifetime, fluorescence polarization, fluorescence anisotropy, or fluorescence correlation), luminescence, phosphorescence, absorbance, singlet-oxygen production, electron spin resonance, radioactivity, nuclear magnetic resonance, and X-ray scattering.

Alternatively, a detectable group may be detected by receptor-binding, protein-protein or protein-nucleic acid crosslinking, or protein or nucleic acid cleavage.

Preferred detectable groups include fluorescent moieties. In one preferred embodiment, cyanine fluorescent moieties are used. These include, but are not limited to: Cy3: 1-R-2-[3-[1-R-1,3-dihydro-3,3-dimethyl-5-sulfo-2H-indol-2-ylidene]-1-propeny 1]-3,3-dimethyl-5-sulfo-3H-indolium, Cy5: 1-R-2-[5-[1-R-1,3-dihydro-3,3-dimethyl-5-sulfo-2H-indol-2-ylidene]-1,3-penta dienyl]-3,3-dimethyl-5-sulfo-3H-indolium, Cy7: 1-R-2-[7-[1-R-1,3-dihydro-3,3-dimethyl-5-sulfo-2H-indol-2-ylidene]-1,3,5-heptatrienyl]-3,3-dimethyl-5-sulfo-3H-indolium, indocyanine green and IRDye (1-R-2-[2-[2-R'-3-[(1-R-1,3-dihydro-3,3-dimethyl-5-sulfo-2H-indol-2-ylidene) ethylidene]-1-cyclohexen-1-yl] ethenyl]-3,3-dimethyl-5-sulfo-3H-indolium), and mono- and non-sulfonated derivatives thereof. In another preferred embodiment, squaraine fluorescent moieties are used.

Examples of the dyes discussed above are described, inter alia, in Southwick et al., 1990, *Cytometry* 11:418-430; Mujumdar et al., 1993, *Bioconjugate Chemistry* 4:105-111; Waggoner and Ernst, *Fluorescent Regents for Flow Cytometry, Part 1: Principles of Clinical Flow Cytometry* (1993) and Haugland, *Molecular Probes Handbook of Fluorescent Probes and Research Chemicals, Molecular* Inc. 6th edition (1996) and Berling and Reiser, *Methoden der Organischer Chemie*, p 231-299 (1972), Oswald et al., *Analytical Biochemistry* 280: 272-277 (2000), Oswald et al. *Photochemistry and Photobiology* 74(2): 237-245 (2001), Oswald et al. *Bioconjugate Chemistry* 10: 925-931 (1999), U.S. Pat. No. 6,086,737. The dye structures in these publications are all incorporated herein by reference.

In a particularly preferred embodiment, the detectable group X in Formula (I) may be selected from the following cyanine detectable groups:

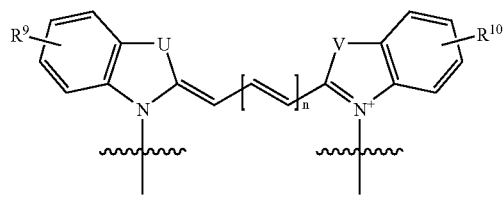
(XII)

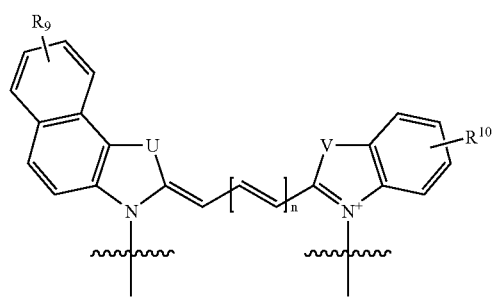
(XIII)

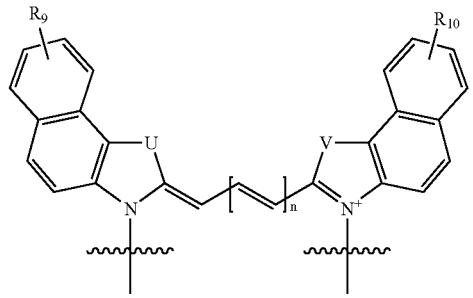
(XIV)

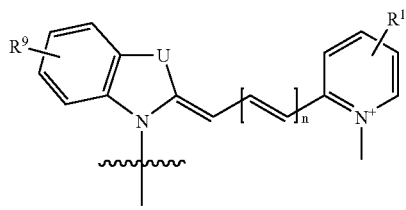
(XV)

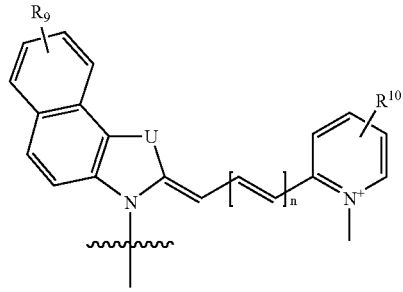
(XVI)

wherein U and V are each independently $C(R^{14})_2$, NH, O, S, or $(CH)_2$; $R^9$ and $R^{10}$ are each independently H or sulfonate; $R^{14}$ is H, $CH_3$, $CH_2CH_3$, or $(CH_2)_2CH_3$; and n is 0 or an integer of from 1 to 6.

In another preferred embodiment, X in Formula (I) may be selected from the following squaraine detectable groups:

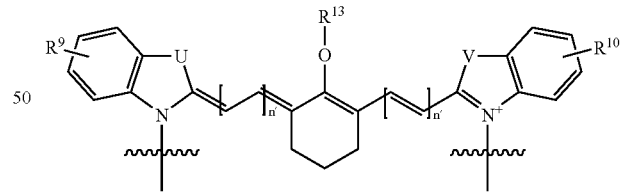
(XVII)

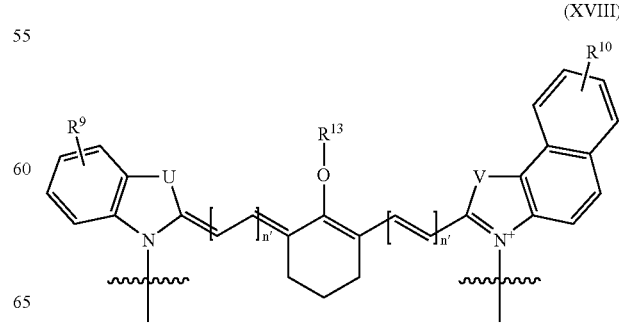
(XVIII)

-continued (XIX)
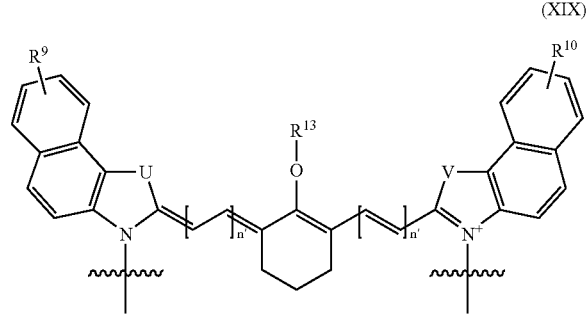

(XX)

(XXI)

(XXII)

(XXIII)

-continued (XXIV)
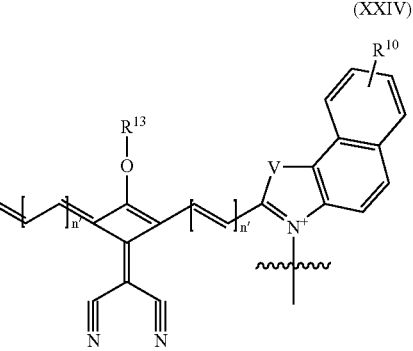

(XXV)
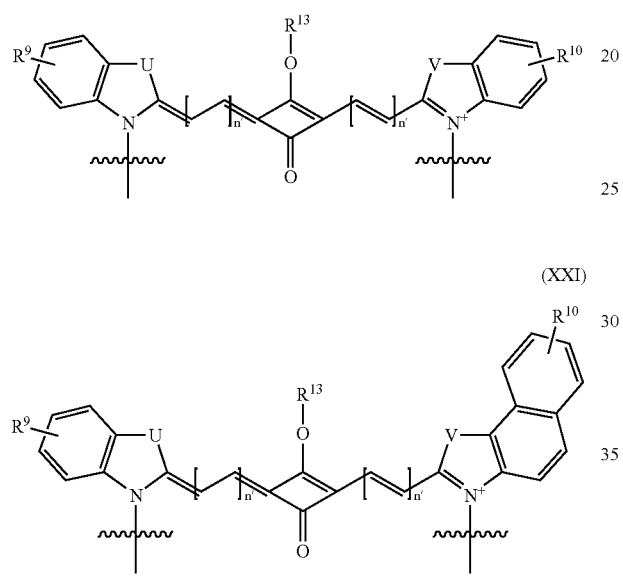

wherein U and V are each independently $C(R^{14})_2$, NH, O, S, or $(CH)_2$; $R^9$ and $R^{10}$ are each independently H or sulfonate; and $R^{13}$ is absent or is selected from the group consisting of H, an alkyl group, and an aryl group; $R^{14}$ is H, $CH_3$, $CH_2CH_3$, or $(CH_2)_2CH_3$; and n' is 0 or an integer of from 1 to 3.

Among the preferred bis-phenylarsine molecules of Formula (I) for use in the present invention are those represented by the following general structural formulae:

(VI)
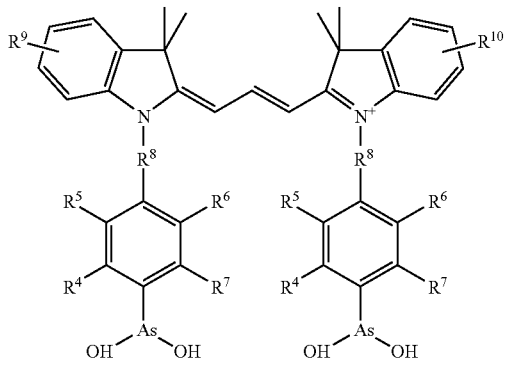

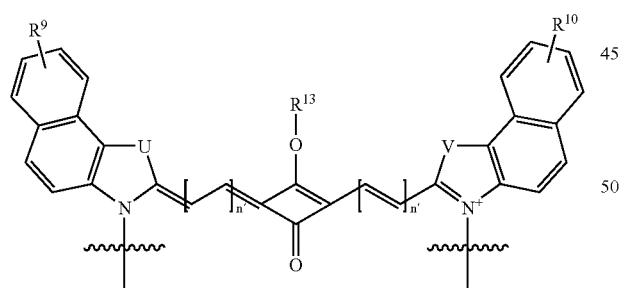

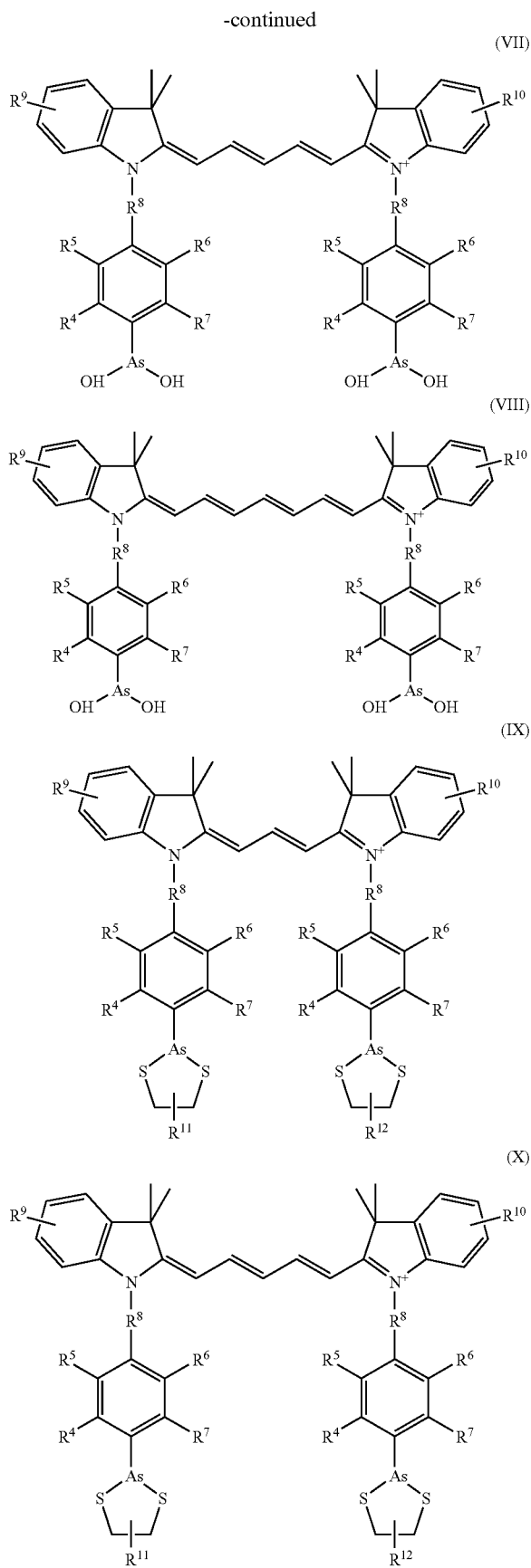

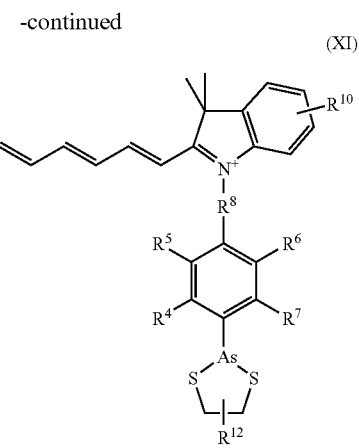

wherein $R^4$, $R^5$, $R^6$ and $R^7$ are each independently H, F, $OR^3$, $R^3$, OAc, $NH_2$, $N(C_1-C_4$ alkyl$)_2$, or $R^4$ with $R^5$, or $R^6$ together with $R^7$, or both, form a ring; wherein $R^3$ is H, $CH(OH)CH_2OH$ or $(CH_2)_q$—Y, wherein q is 1-4, and Y is H, OH, $NH_2$, SH, COOH, OAc, $CONH_2$ or CN; and wherein $R^8$ is a linear or branched optionally substituted spacer having a length from about 1.5 to about 15 Ångstroms; $R^9$ and $R^{10}$ are each independently selected from the group consisting of H and sulfonate; and $R^{11}$ and $R^{12}$ are each independently selected from the group consisting of H and alkylsulfonate. Preferably, $R^{11}$ and $R^{12}$ are each $CH_2SO_3$ or $CH_2CH_2SO_3$.

Among the preferred bis-phenylarsine molecules of Formula (II) for use in the present invention are those in which the detectable group is fluorescein, resorufin or derivatives thereof. For example, one preferred bis-phenylarsine molecule according to Formula (II) is 4',5'-bis (1,3,2-dithioarsolan-2-yl)fluorescein, referred to as FlAsH-EDT$_2$ (fluorescein arsenical helix binder, bis-EDT adduct):

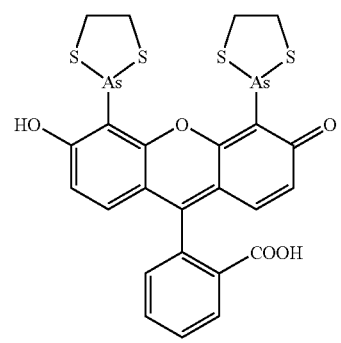

This initially non-fluorescent molecule develops bright fluorescence with the addition of a tetracysteine peptide to displace the EDT and is described by Griffin, et al. in Science (1998) 281:269-271.

Another preferred bis-phenylarsine molecule according to Formula (II) is ReAsH-EDT$_2$.

This molecule is described by Adams, et al. in J. Am. Chem. Soc. (2002) 124, 6063-6076, and its structure is shown below:

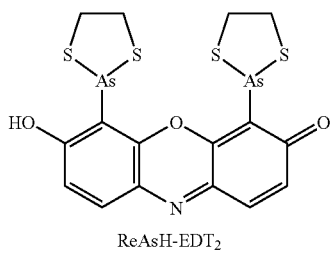

ReAsH-EDT$_2$

Modifying groups that aid in the use of the bis-phenylarsine derivatives may also be incorporated. For example, the bis-phenylarsine derivative according to Formula (I) or Formula (II) may be substituted at one or more positions to add a solid-phase binding group or a crosslinking group.

For applications involving labeling of target materials within living cells, the bis-phenylarsine derivative preferably is capable of traversing a biological membrane. Smaller molecules are generally able to traverse a biological membrane better than larger derivatives. Bis-phenylarsine derivatives of less than 2000 Daltons are preferable for membrane traversal.

The polarity of the bis-phenylarsine derivative can also determine the ability of the bis-phenylarsine derivative to traverse a biological membrane. Generally, a hydrophobic bis-phenylarsine derivative is more likely to traverse a biological membrane. The presence of polar groups can reduce the likelihood of a molecule to traverse a biological membrane. A bis-phenylarsine derivative that is unable to traverse a biological membrane may be further derivatized by addition of groups that enable or enhance the ability of the molecule to traverse a biological membrane. Preferably, such derivatization does not significantly alter the ability of the bis-phenylarsine derivative to subsequently react with a target sequence. The bis-phenylarsine derivative may also be derivatized transiently. In such instances, after traversing the membrane, the derivatizing group is eliminated to regenerate the original bis-phenylarsine derivative. Examples of derivatization methods that increase membrane traversability include ether formation with acyloxyalkyl groups. For example, an acetoxymethyl ether is readily cleaved by endogenous mammalian intracellular esterases. Jansen, A. and Russell, T. J., *J. Chem. Soc.*, 2127-2132 (1965). Also, pivaloyl ester is useful in this regard. Madhu et al., *J. Occul. Pharmaco. Ther.*, 14:389-399 (1998).

Methods of Synthesis of Compositions Employed in the Invention

Compounds According to Formula (I)

Methods of synthesis of compounds according to Formula (I) were previously described in copending, commonly owned U.S. application Ser. No. 10/461,224, the entire contents of which are incorporated herein by reference. Compounds containing a non-sulfonated cyanine or squaraine detectable group, involve coupling of:

(a) a synthon selected from mono-phenylarsine-functionalized 2,3,3-trimethylindole, mono-phenylarsine-functionalized 2,3,3-trimethylbenzindole, mono-phenylarsine-functionalized 2-methyl-pyridine, mono-phenylarsine-functionalized 2-methyl-benzothiazole, mono-phenylarsine-functionalized 2-methyl-napthothiazole, mono-phenylarsine-functionalized 2-methyl-benzoxazole, and mono-phenylarsine-functionalized 2-methyl-napthoxazole;

(b) a synthon, identical or nonidentical to the synthon in (a), selected from the group in (a); and (c) a synthon containing at least one carbon atom.

Methods of synthesis of compounds containing a di-sulfonated cyanine or squaraine detectable group, involve coupling of:

(a) a synthon selected from mono-phenylarsine-functionalized 2,3,3-trimethyl-5-sulfanato-indole, mono-phenylarsine-functionalized 2,3,3-trimethyl-6-sulfanato-benzindole, mono-phenylarsine-functionalized 2-methyl-5-sulfanato-pyridine, mono-phenylarsine-functionalized 2-methyl-5-sulfanato-benzothiazole, mono-phenylarsine-functionalized 2-methyl-6-sulfanato-napthothiazole, mono-phenylarsine-functionalized 2-methyl-5-sulfanato-benzoxazole, and mono-phenylarsine-functionalized 2-methyl-6-sulfanato-napthoxazole;

(b) a synthon, identical or nonidentical to the synthon in (a), selected from the group in (a); and (c) a synthon containing at least one carbon atom.

Methods of synthesis of compounds containing a mono-sulfonated cyanine or squaraine detectable group, involve coupling of:

(a) a synthon selected from mono-phenylarsine-functionalized 2,3,3-trimethylindole, mono-phenylarsine-functionalized 2,3,3-trimethylbenzindole, mono-phenylarsine-functionalized 2-methyl-pyridine, mono-phenylarsine-functionalized 2-methyl-benzothiazole, mono-phenylarsine-functionalized 2-methyl-napthothiazole, mono-phenylarsine-functionalized 2-methyl-benzoxazole, and mono-phenylarsine-functionalized 2-methyl-napthoxazole;

(b) a synthon selected from mono-phenylarsine-functionalized 2,3,3-trimethyl-5-sulfanato-indole, mono-phenylarsine-functionalized 2,3,3-trimethyl-6-sulfanato-benzindole, mono-phenylarsine-functionalized 2-methyl-5-sulfanato-pyridine, mono-phenylarsine-functionalized 2-methyl-6-sulfanato-benzothiazole, mono-phenylarsine-functionalized 2-methyl-6-sulfanato-napthothiazole, mono-phenylarsine-functionalized 2-methyl-5-sulfanato-benzoxazole, and mono-phenylarsine-functionalized 2-methyl-6-sulfanato-napthoxazole; and (c) a synthon containing at least one carbon atom.

Coupling of the synthons referred to herein can be accomplished in a single step, or in two steps. For example, for symmetric compounds (i.e., where (a) and (b) are identical), coupling of the reactants (a), (b), and (c) desirably is carried out in a single step. For asymmetric compounds (i.e., where (a) and (b) are non-identical), coupling of reactants (a), (b), and (c) desirably is carried out in two steps: i.e., reaction of (a) with (c), followed by reaction of the resultant product with (b); or, alternatively, reaction of (b) with (c), followed by reaction of the resultant product with (a).

Coupling of the synthons referred to herein can be performed in solution, or with one or more synthons attached to a solid support.

Coupling of the synthons referred to herein can be performed with the phenylarsine moiety in an unprotected form, or with the chelator in a protected form initially and optionally deprotected thereafter.

Compounds According to Formula (II)

Methods of synthesis of bis-phenylarsine compounds according to Formula (II) have previously been described in U.S. Pat. Nos. 6,008,378 and 6,451,569B1 to Tsien, et al., the entire contents of which are incorporated herein by reference, and are further described by Griffin, et al. in Science 281:269-272 (1998). Methods for synthesizing ReAsH compounds have been described by Adams, et al. in J. Am. Chem. Soc. (2002) 124, 6063-6076, which is incorporated herein by reference.

Target Materials and Peptide Tags Employed in the Present Invention

The invention provides detectable complexes of at least two different labels with at least two different peptide tags. Detectable complexes as used herein refer to the association between the peptide tags bound to the at least one target material and the bis-phenylarsine molecules.

Two or more bis-phenylarsine molecules according to Formula (I) can be employed as labels, wherein the mean distance and/or mean angle between the two pendant phenylarsine moieties in one of the molecules is distinct from the mean distance and/or mean angle between the phenylarsine moieties in the other of the molecules. Alternatively, at least one bis-phenylarsine molecule according to Formula (I) can be employed in combination with at least one bis-phenylarsine molecule according to Formula (II), wherein one or more of the positions in Formula (II) has been substituted with a detectable group. In the present invention, the mean distance and/or mean angle between the two pendant phenylarsine moieties in the Formula (I) molecule is distinct from the mean distance and/or mean angle between the phenylarsine moieties in the Formula (II) molecule. In one embodiment, the mean distance and/or mean angle between the pendant phenylarsine moieties in the first conjugate is at least about 1.5 Angstroms greater than the mean distance and/or mean angle between the pendant phenylarsine moieties in the second conjugate.

It is possible, for example, to change the mean distance and/or mean angle between the two pendant phenylarsine moieties in Formula (I) by changing the value for n in a cyanine detectable X group according to Formulae (XII-XVI) or by changing the value for n' in a squaraine detectable X group according to Formulae (XVII-XXV). This is not possible with a molecule of Formula (II) because the two pendant phenylarsine moieties are fixed in a precisely defined spacial relationship.

Suitable target materials include, but are not limited to: polypeptides, and polypeptide mimetics (such as peptide nucleic acid). Preferably, the target material is a polypeptide.

As used herein, "polypeptide" refers to both short chains, commonly referred to as "peptides, "oligopeptides," or "oligomers," and to longer chains, generally referred to as "proteins." Polypeptides may contain amino acids other than the 20 gene-encoded amino acids. Polypeptides may include amino acid sequences modified either by natural processes, such as post-translational processing, or by chemical modification techniques which are well-known in the art. Such modifications are well described in basic texts and in more detailed monographs, as well as in research literature. Thus "polypeptide" includes peptides, oligopeptides, polypeptides and proteins, all of which terms are used interchangeably herein.

The bis-phenylarsine moieties of molecules according to Formula (I) or (II) bond with a target material containing, or derivatized to contain, a tetracysteine-containing target sequence, herein referred to interchangeably as a "target sequence" or a "tag." The As atoms of the bis-phenylarsine moieties bond with S atoms of the target sequence. In the detectable complex of the present invention, at least two different peptide tags (i.e., first and second peptide tags), which can be located collectively on one or more target materials, preferentially associate with one or the other of at least two different labels (i.e., the first and second conjugates). In one embodiment of the detectable complex of the present invention, the first peptide tag is bound to a first target material and the second peptide tag is bound to a second target material. In a further embodiment, the detectable complex of the present invention can further include a third peptide tag bound to the at least one target material; and a third conjugate having a detectable group and two pendant phenylarsine moieties comprising a third tag binding group, wherein the mean distance and/or mean angle between the pendant moieties in the third conjugate is different from that in the first conjugate.

In one embodiment of the compositions and methods of the present invention, at least one of the first and second conjugates is represented by the general Formula (I) and tautomers, acids and salts thereof. For example, each of the first and second conjugates in the compositions and methods of the present invention can be represented by the general structural Formula (I) and tautomers, acids and salts thereof. In this instance, each of the first and second peptide tags is preferably of the form $C(X)_iC(X)_jC(X)_kC$, wherein C is cysteine, X is any amino acid, i, j and k are each independently 0 or an integer of from 1 to 8. The values of X, i, j and k for the first peptide tag on the at least one target material can be such that the first peptide tag interacts tightly with the first conjugate, but does not interact, or interacts less tightly with the second conjugate. Likewise, the values of X, i, j and k for the second peptide tag on the at least one target material can be such that the second peptide tag interacts tightly with the second conjugate, but does not interact, or interacts less tightly with the first conjugate.

In one embodiment, at least one of the first and second peptide tags is of the form $CC(P)_nCC$, wherein C is Cysteine; P is Proline; and n is an integer from 3 to 8. For example, at least one of the first and second peptides can desirably be selected from the following: CCPPPCC (SEQ ID NO: 1); CCPPPPCC(SEQ ID NO: 2); CCPPPPPCC (SEQ ID NO: 3); CCPPPPPPCC (SEQ ID NO: 4); and CCPGPCC (SEQ ID NO: 5). In another embodiment, at least one of the first and second peptide tags is CCGPCC (SEQ ID NO: 6). In yet another embodiment, at least one of the first and second peptide tags is selected from the following: CGCGCGC (SEQ ID NO:7), CGPCCGPC (SEQ ID NO: 8), CGPCGCGPC (SEQ ID NO: 9) and CGPCG-GCGPC SEQ ID NO: 10).

In one preferred embodiment, at least one of the peptide tags has the general form CCXXCC, wherein C is cysteine and X is any amino acid, an example of which is CCGPCC (SEQ ID NO: 6). This tag has been found by the present inventors to interact tightly with Cy3 derivatives of conjugates according to Formula (I), and to not interact, or interact less tightly with Cy5 derivatives of conjugates according to Formula (I).

Thus, in one preferred embodiment, a first peptide tag is of the form CCXXCC, wherein C is Cysteine and X is any amino acid, and the first conjugate is a Cy3 derivative selected from the following: Cy3 bis-propionamido-phenylarsineoxide, Cy3 bis-propionamido-phenylarsine-ethanedithiol, Cy3 bis-sulfonato bis-propionamido-phenylarsine-ethanedithiol, and Cy3 bis-sulfonato bis-propionamido-phenylarsine-propanedithiol-sulfonic acid. In a more preferred embodiment, the first peptide tag is CCGPCC (SEQ ID NO: 6); and the first conjugate is selected from Cy3 bis-propionamido-phenylarsine-ethanedithiol or Cy3 bis-sulfonato bis-propionamido-phenylarsine-ethanedithiol.

In another preferred embodiment, the first peptide tag is of the form CCXXCC, wherein C is Cysteine and X is any amino acid, which preferentially associates with a first conjugate selected from Cy3 bis-propionamido-phenylarsineoxide, Cy3 bis-propionamido-phenylarsine-ethanedithiol, Cy3 bis-sulfonato bis-propionamido-phenylarsine-ethanedithiol, and Cy3 bis-sulfonato bis-propionamido-phenylarsine-propanedithiol-sulfonic acid; and the second peptide tag is of the form: CXX(X)$_j$CXXC, wherein j is 0 or an integer from 1 to 8, which preferentially associates with a second conjugate selected from Cy5 bis-propionamido-phenylarsineoxide, Cy5 bis-propionamido-phenylarsine-ethanedithiol, Cy5 bis-sulfonato bis-propionamido-phenylarsine-ethanedithiol, and Cy5 bis-sulfonato bis-propionamido-phenylarsine-propanedithiol-sulfonic acid. More preferred, the second peptide tag has the form CGPC(G)$_j$CGPC, wherein j is 0 or an integer from 1 to 8. Particularly preferred are embodiments where the second peptide tag is CGPCCGPC (SEQ ID NO: 8), CGPCGCGPC (SEQ ID NO: 9) or CGPCGGCGPC (SEQ ID NO: 10); and the second conjugate is Cy5 bis-propionamido-phenylarsine-ethanedithiol or Cy5 bis-sulfonato bis-propionamido-phenylarsine-ethanedithiol. Further desired are embodiments in which the second peptide tag is CGCGCGC (SEQ ID NO: 7); and the second conjugate is Cy5 bis-propionamido-phenylarsine-ethanedithiol or Cy5 bis-sulfonato bis-propionamido-phenylarsine-ethanedithiol.

In particularly preferred embodiments of the compositions and methods of the present invention, the first conjugate is represented by the general structural Formula (I) and tautomers, acids and salts thereof; and the second conjugate is represented by the general structural Formula (II) and tautomers, anhydrides and salts thereof, wherein Formula (II) has been substituted at one or more positions with a detectable group, such as fluorescein, resorufin or derivatives thereof. The present inventors have surprisingly found that certain peptide tags interact with a conjugate represented by Formula (I), but do not interact substantially with a conjugate represented by Formula (II). This allows for multi-site-specific labeling of target materials, which results in defined multi-labeled products with highly desirable properties.

For example, a first peptide tag that interacts with a first conjugate represented by Formula (I), but that does not interact substantially with a second conjugate represented by Formula (II) may be of the form C(X)$_i$C(X)$_j$C(X)$_k$C, wherein C is cysteine, X is any amino acid, i, j and k are each independently 0 or an integer of from 1 to 8. In a preferred embodiment, the first peptide tag has a sequence of the form CC(P)$_n$CC, wherein C is Cysteine; P is Proline; and n is an integer from 3 to 8. In a more preferred embodiment, the first peptide tag is selected from the following: CCPPPCC (SEQ ID NO: 1); CCPPPPCC (SEQ ID NO: 2); CCPPPPPCC (SEQ ID NO: 3); CCPPPPPPCC (SEQ ID NO: 4); and CCPGPCC (SEQ ID NO: 5). Each of these tags has been found by the present inventors to bind to the following derivatives of a conjugate having Formula (I), but to not interact substantially with FlAsH-EDT$_2$: Cy3 bis-sulfonato bis-propionamido-phenylarsine, Cy3 bis-propionamido-phenylarsine, Cy5 bis-sulfonato bis-propionamido-phenylarsine and Cy5 bis-propionamido-phenylarsine.

In another preferred embodiment, the first peptide tag is selected from CGCGCGC (SEQ ID NO: 7) and CGPC-CGPC (SEQ ID NO: 8). Each of these has been found by the present inventors to interact with a first conjugate of Formula (I), but to not interact substantially with a second conjugate of Formula (II). In particular, the present inventors have found that tags CGCGCGC (SEQ ID NO: 7) and CGPCCGPC (SEQ ID NO: 8) bind to Cy5 bis-sulfonato bis-propionamido-phenylarsine or Cy5 bis-propionamido-phenylarsine, but do not interact substantially with FlAsH-EDT$_2$.

In a most preferred embodiment, the first peptide tag interacts with a first conjugate represented by Formula (I) and is of the aforementioned form C(X)$_i$C(X)$_j$C(X)$_k$C, wherein C is cysteine, X is any amino acid, i, j and k are each independently 0 or an integer of from 1 to 8; and the second peptide tag interacts with a second conjugate represented by Formula (II) and is of the form C(X)$_i$C, wherein X is any amino acid and i is 0-6. In one desired embodiment, the second peptide tag is selected from the following: CCCC (SEQ ID NO: 11) or CCGCC (SEQ ID NO: 12). As described above, the conjugate represented by Formula (II) is substituted at one or more positions in Formula (II) with a detectable group, which in one preferred embodiment is a fluorescent moiety.

The target sequence (i.e., tag) may be incorporated at any desired site, or set of sites, within a target material, but preferably is incorporated at a site that is (a) accessible and (b) not essential for structure and function of the target material.

For example, when the target material is a protein, the target sequence preferably is incorporated at the N-terminal region, at the C-terminal region, at an internal loop region, at a surface-exposed non-essential loop, at an internal linker region, or at combinations thereof. The specific site, or set of sites, can be chosen to accommodate the functional requirements of a protein. For example, it is known that N-terminal modification of chemokines can affect their activity; therefore, in applications with chemokines, either C-terminal modification or internal modification would be preferable. Since labeling is performed at defined, user-selected sites, effects on the activity of target material can be avoided. When it is important to preserve the activity of the tagged target material, specific activity testing of the tagged vs. the untagged target material may be conducted to verify activity. See, for example, Mas et al,. *Science*, 233:788-790 (1986).

Target-sequence-containing polypeptides may be generated by total synthesis, partial synthesis, in vitro translation, or in vivo bacterial, archaeal, or eukaryotic production.

In one preferred embodiment, the target sequences and/or target-sequence-containing polypeptides used in the invention are prepared using solid-phase synthesis (see, e.g., Merrifield et al. *J. Am. Chem. Soc.*, 85:2149, (1962) Steward and Young, *Solid Phase Peptides Synthesis*, Freeman, San Francisco, (1969), and Chan and White, *Fmoc Solid Phase Peptide Synthesis—A Practical Approach*, Oxford Press (2000)).

In another preferred embodiment, the target sequences and/or target-sequence-containing polypeptides used in the invention are prepared using native chemical ligation (Dawson et al., *Science*, 266, 1994).

In an especially preferred embodiment, the target sequences and/or target-sequence-containing polypeptides are generated by in vivo bacterial, archaeal, or eukaryotic expression of a recombinant nucleic acid sequence encoding the target-sequence-containing polypeptide(s). Methods for the construction of recombinant nucleic acid sequences encoding a tag-containing polypeptide are well known in the art (Sambrook and Russel, *Molecular Cloning A Laboratory Manual*, 3$^{rd}$ Ed., Cold Spring Harbor Laboratory, New York (2001), the entirety of which is herein incorporated by reference. In addition, techniques for transient or stable introduction of recombinant nucleic acid sequences into living cells (see, for example, Ausubel et al., *Current Protocols In Molecular Biology*, John Wiley & Sons, Inc. (1995)), for replacement of native nucleic acid sequences by recombinant nucleic acid sequences in living cells (see, for example, Ausubel et al., *Current Protocols In Molecular Biology*, John Wiley & Sons, Inc. (1995)), and for expression of recombinant nucleic acid sequences in living cells (see e.g., Lee and Arthans, H. J. *Biol. Chem.*, 263:3521, (1988); Rosenberg, et al., *Gene*, 56:125 (1987)), are well known in the art.

Labeling is accomplished by contacting at least two different bis-phenylarsine derivatives with at least one target-sequence-containing target material. A first target sequence (i.e., peptide tag) is bound to the at least one target material; and a second peptide tag is bound to the at least one target material. The bis-phenylarsine derivatives may be contacted with target-sequence-containing target material located, for example, in a test tube, a microtiter-plate well, or immobilized on a solid-phase. Alternatively, the bis-phenylarsine derivatives may be contacted with target-sequence-containing target material located within a cell, tissue, organ, or organism (in which embodiment, the bis-phenylarsine derivatives preferably are capable of traversing an intact biological membrane).

In one preferred embodiment, the bis-phenylarsine molecules described herein are used to label target-sequence-containing molecules within living cells. The bis-phenylarsine molecules employed in this invention may be introduced into cells by diffusion (for bis-phenylarsine derivatives capable of traversing biological membranes) or by microinjection, electroporation, or vesicle fusion (for any bis-phenylarsine derivative). The target-sequence-containing molecules may be introduced into cells by microinjection, electroporation, or vesicle fusion, or by expression of recombinant genes in situ.

In one especially preferred embodiment, target-sequence-containing protein produced by expression of a recombinant gene within living cells is reacted with the at least two different bis-phenylarsine molecules (i.e., the first and second conjugates) by incubating cells in medium containing the conjugates. Following labeling, and optionally following further manipulations, cells are imaged using an epi-illumination, confocal, or total-internal-reflection optical microscope with an optical detector, such as a CCD camera, an intensified CCD camera, a photodiode, or a photomultiplier tube, and fluorescence signals are analyzed.

Uses of the Compositions of the Invention

It is contemplated that the detectable complexes of the invention may be used in a variety of in vitro and in vivo applications.

The detectable complexes of the invention may be used in numerous standard assay formats, as are well known in the art. Some examples of assay formats include fluorescence emission intensity, fluorescence polarization (FP), fluorescence anisotropy (FA), fluorescence resonance energy transfer (FRET), fluorescence correlation spectroscopy (FCS), fluorescence-activated cell—or particle—sorting (FACS), x/y-fluorescence scanning (FluorImaging), epi-illumination optical microscopy, confocal optical microscopy, total-internal-reflection optical microscopy, absorbance spectroscopy, enzyme-linked immunosorbent assay (ELISA), radioimmunoassay (RIA), scintillation proximity assay (SPA), autoradiography, and assays formats that involve use of biotin or other hapten incorporation to provide a recognition event for binding or immobilization of one or more components.

Some examples, which are intended to be illustrative and not limiting of possible assay formats and applications that could use multi-site specific bis-phenylarsine-labeled target materials, are set forth below.

For example, the bis-phenylarsine derivatives of the present invention may be used to detect and/or quantify at least one polypeptide of interest containing, or derivatized to contain, at least two different peptide tags. In one embodiment, a first peptide tag is bound to a first polypeptide and a second peptide tag is bound to a second polypeptide. The at least one polypeptide containing the peptide tags is incubated with the following under suitable conditions and for a period of time sufficient to allow labeling thereof: (i) a first conjugate having a detectable group and two pendant phenylarsine moieties comprising a first tag binding group; wherein the first conjugate preferentially associates with the first peptide tag; and (ii) a second conjugate having a detectable group and two pendant phenylarsine moieties comprising a second tag binding group; wherein the second conjugate preferentially associates with the second peptide tag. The first and second conjugates are different in that the mean distance and/or mean angle between the pendant phenylarsine moieties in the first conjugate is different from the mean distance and/or mean angle between the pendant phenylarsine moieties in the second conjugate.

Labeled polypeptide(s) optionally may be separated from unbound material before the detection step using any method known in the art, and the detectable groups are detected, thereby detecting the polypeptide of interest. The at least one polypeptide containing the peptide tags may be included in any material, including, but not limited to, cuvettes, microtiter plates, capillaries, flow cells, test tubes, gels, blots, and biological samples.

In one embodiment of the labeling method, the first and second conjugates are each represented by the general structural Formula (I) and tautomers, acids and salts thereof, wherein the detectable group X in Formula (I) is a fluorescent moiety. In this instance, each of the first and second tags is preferably of the form $C(X)_iC(X)_jC(X)_kC$, wherein C is cysteine, X is any amino acid, and i, j, and k are each independently selected from 0 or an integer from 1-8. Suitable examples are described above.

In another embodiment of the labeling method, the first conjugate is represented by the general structural Formula (I) and tautomers, acids and salts thereof, wherein X in Formula (I) is a fluorescent moiety; and the second conjugate is represented by the general structural Formula (II) and tautomers, anhydrides and salts thereof, wherein one or more positions of Formula (II) are substituted so as to add a fluorescent moiety. Desirably, the first peptide interacts with the first conjugate represented by Formula (I), but does not interact substantially with the second conjugate represented by Formula (II). In this instance, the first peptide is preferably of the form $C(X)_iC(X)_jC(X)_kC$, wherein C is cysteine, X is any amino acid, and i, j, and k are each independently selected from 0 or an integer from 1-8; and the second peptide tag is of the form $C(X)_iC$, wherein X is any amino acid and i is 0-6. Suitable examples are provided above.

In one embodiment, the reacting and/or detecting step is performed in a gel matrix. In another embodiment, the reacting and/or detecting step is performed in a complex mixture of components.

The invention also provides an assay method for monitoring a binding process. In this method, a first component of a specific reaction pair is reacted with a second component of the pair. Examples of specific reaction pairs include, but are not restricted to, antibodies/antigens, hormone/receptor, enzyme/substrate, and protein/analyte. The pair has bound thereto a first peptide tag and a second peptide tag, which are different. Moreover, the pair is labeled with at least two different labels. The two different labels are the following: (i) a first conjugate having a detectable group and two pendant phenylarsine moieties comprising a first tag binding group; wherein the first conjugate preferentially associates with the first peptide tag; and (ii) a second conjugate having a detectable group and two pendant phenylarsine moieties comprising a second tag binding group; wherein the second conjugate preferentially associates with the second peptide tag. The first and second conjugates are different in that the mean distance and/or mean angle between the pendant phenylarsine moieties in the first conjugate is different from the mean distance and/or mean angle between the pendant phenylarsine moieties in the second conjugate. The reaction can be monitored by monitoring a change in a property of the detectable group on at least one the first and second conjugates in the presence of both components of the pair, as compared to in the presence of only one of the components of the pair. In one embodiment, a change in property indicates that the first and second components bind to each other.

In one embodiment of the assay for monitoring a binding process, the first component has bound thereto the first tag, and the second component has bound thereto the second tag. In another embodiment, the first component has bound thereto the first and second tags. In yet another embodiment, the second component has bound thereto the first and second tags.

In one embodiment of the assay for monitoring a binding process, at least one of the first and second conjugates is represented by Formula (I) and tautomers, acids and salts thereof, wherein X is a fluorescent moiety. In another embodiment, the first conjugate is represented by the general structural Formula (I) and tautomers, acids and salts thereof, wherein X in Formula (I) is a fluorescent moiety; and the second conjugate is represented by the general structural Formula (II) and tautomers, anhydrides and salts thereof, wherein one or more positions of Formula (II) are substituted so as to add a fluorescent moiety.

In a further embodiment of the assay for monitoring a binding process, at least one of the first and second conjugates includes a fluorescent moiety as the detectable group and the other of the first and second conjugates includes a fluorescent moiety or a chromophore as the detectable group. The monitoring step can include detecting a fluorescence property associated with the fluorescent moiety on at least one of the first and second conjugates. The fluorescence property can be selected from the following: a fluorescence-emission intensity, a fluorescence lifetime, a fluorescence polarization, a fluorescence anisotropy, a fluorescence correlation and combinations thereof.

For example, a first component of a specific binding pair can be labeled with a molecule according to Formula (I), wherein X in Formula (I) is a fluorochrome; and a second component of the pair can be labeled with a molecule according to Formula (II), wherein the detectable group placed at one or more of the positions in Formula (II) is a fluorochrome or chromophore capable of participating in a fluorescence energy transfer, fluorescence quenching, or exciton formation with X. The reaction can be monitored by monitoring a fluorescent property of X. The conjugates differ in the mean distance and/or mean angle between the pendant phenylarsine moieties.

Alternatively, a first component of a specific binding pair can be labeled with a molecule according to Formula (I), wherein X in Formula (I) is a fluorochrome or chromophore; and the second component of the pair can be labeled with a different molecule according to Formula (II), wherein the detectable group placed at one or more of the positions of Formula (II) is a fluorochrome which is able to participate in fluorescence energy transfer, fluorescence quenching, or exciton formation with the detectable group on Formula (I). The reaction can be monitored by monitoring a fluorescent property of the fluorochrome on the second conjugate.

In a fluorescence-emission-intensity assay, the sample is exposed to light of a first wavelength (able to be absorbed by a fluorescent moiety), and fluorescence-emission intensity is monitored at a second wavelength (emitted by said fluorescent moiety). Fluorescence-emission intensity is dependent on the quantity of the fluorescent moiety and on the local environment of the fluorescent moiety.

A fluorescence-emission-intensity assay to detect and quantify binding between two molecules, molecule 1 and molecule 2, having bound thereto at least two different peptide tags may be configured as follows: A reaction mixture is prepared by combining: (i) molecule 1 labeled with a first conjugate comprising a fluorescent moiety X and (ii) molecule 2 labeled with a second conjugate, wherein the detectable group is a fluorochrome or chromophore that can react with X. The first and second conjugates can be, for example, according to Formula (I) and Formula (II), respectively, and differ in the mean distance and/or mean angle between the pendant phenylarsine moieties. Complex formation (i.e., the association of the labels with the tag-containing molecules) results, directly or indirectly, in a change in the local environment of X, and, correspondingly, in a change in the fluorescence emission intensity of X. The progress of the reaction is monitored by observing the change in fluorescence emission intensity of X. Equilibrium association and dissociation constants may be extracted from the concentration-dependence of the reaction.

In a fluorescence-polarization (FP) or fluorescence-anisotropy (FA) assay, a sample is exposed to polarized light of a first wavelength (able to be absorbed by a fluorescent moiety), and fluorescence-emission polarization or anisotropy is monitored at a second wavelength (emitted by said fluorescent moiety). Fluorescence-emission polarization or anisotropy is inversely related to the rotational dynamics, and thus to the size, of the fluorescent moiety (or, if the fluorescent moiety is attached to a molecule or complex, to the rotational dynamics, and thus to the size, of the molecule or complex). FP or FA assays permit detection of reactions that result in changes in size of molecules or complexes, including especially, macromolecule-association and macromolecule-dissociation reactions.

An FP or FA assay to detect and quantify binding between two molecules, molecule 1 and molecule 2, having bound thereto at least two different peptide tags may be configured as follows: A reaction mixture is prepared by combining (i) molecule 1 labeled with a first conjugate comprising a fluorescent moiety X and (ii) molecule 2 labeled with a second conjugate, wherein the detectable group is a fluorochrome or chromophore that can react with X. The first and second conjugates can be, for example, according to Formula (I) and Formula (II), respectively, and differ in the mean distance and/or mean angle between the pendant phenylarsine moieties. Complex formation results in formation of a higher-molecular-weight, higher-FP, higher-FA species. The progress of the reaction is monitored by observing the decrease in FP or FA. Equilibrium association and dissociation constants are extracted from the concentration-dependence of the reaction.

A further FP or FA assay may be used to detect and quantify proteolytic activity and may be configured as follows: A reaction mixture is prepared by combining: (i) a substrate molecule labeled with first and second conjugates (for e.g., of Formula (I) and Formula (II), respectively, and differing in the mean distance and/or mean angle between the pendant phenylarsine moieties), wherein at least one of these conjugates includes a fluorochrome X as the detectable group and (ii) a sample containing a proteolytic enzyme. Cleavage of the substrate molecule by the proteolytic enzyme results in the production of lower-molecular-weight, lower-FP), lower-FA fragments. The progress of the reaction is monitored by observing the decrease in FP or FA.

Fluorescence resonance energy transfer (FRET) is a physical phenomenon that permits measurement of distance). FRET occurs in a system having a fluorescent probe serving as a donor and a second fluorescent probe serving as an acceptor, where the emission spectrum of the donor overlaps the excitation spectrum of the acceptor. In such a system, upon excitation of the donor with light of the donor excitation wavelength, energy can be transferred from the donor to the acceptor, resulting in excitation of the acceptor and emission at the acceptor emission wavelength. FRET readily can be detected—and the efficiency of FRET readily can be quantified—by exciting with light of the donor excitation wavelength and monitoring emission of the donor, emission of the acceptor, or both. The efficiency of energy transfer, E, is a function of the Förster parameter, $R_o$, and of the distance between the donor and the acceptor, R:

$$E = [1 + (R/R_o)^6]^{-1}$$

wherein the Förster parameter (in Ångstroms, Å), is:

$$R_0 (\text{in Å}) = (0.211 \times 10^{-5})(n^{-4} Q_D \kappa^2 J)^{1/6}$$

wherein n is the refractive index of the medium, $Q_D$ is the donor quantum yield in the absence of the acceptor, $\kappa^2$ is the orientation factor relating the donor acceptor transition dipoles, and J is the spectral overlap integral of the donor emission spectrum and the acceptor excitation spectrum.

If one performs FRET experiments under conditions where $R_o$ is constant, measured changes in E permit detection of changes in R, and, if one performs experiments under conditions where $R_o$ is constant and known, the measured absolute magnitude of E permits determination of the absolute magnitude of R.

With fluorochromes and chromophores known in the art, FRET is useful over distances of about 1 nm to about 15 nm, which are comparable to the dimensions of biological macromolecules and macromolecule complexes. Thus, FRET is a useful technique for investigating a variety of biological phenomena that produce changes in molecular proximity. When FRET is used as a detection mechanism, colocalization of proteins and other molecules can be imaged with spatial resolution beyond the limits of conventional optical microscopy.

A FRET assay to detect and quantify binding between two molecules, molecule 1 and molecule 2, may be configured as follows: A reaction mixture is prepared by combining: (i) molecule 1 labeled with a first conjugate including a detectable fluorescent moiety X and (ii) molecule 2 labeled with a second conjugate including a fluorescent moiety Y or a chrompohore Y as a detectable group, wherein X and Y are able to participate in FRET. The first and second conjugates can be, for example, according to Formula (I) and Formula (II), respectively, and differ in the mean distance and/or mean angle between the pendant phenylarsine moieties. Complex formation results in increased proximity between X and Y, and, correspondingly, in increased FRET. The progress of the reaction is monitored by observing the increase in FRET. Equilibrium association and dissociation constants may be extracted from the concentration-dependence of the reaction.

A FRET assay to detect and quantify proteolytic activity may be configured as follows: A reaction mixture is prepared by combining: a) a substrate molecule labeled at site 1 with a first conjugate including a detectable fluorescent moiety X and labeled at site 2 with a second conjugate including fluorochrome Y as a detectable group, wherein sites 1 and 2 are on opposite sides of the proteolytic-cleavage site, and wherein X and Y are able to participate in FRET; and b) a sample containing a proteolytic enzyme. The first and second conjugates can be, for example, according to Formula (I) and Formula (II), respectively, and differ in the mean distance and/or mean angle between the pendant phenylarsine moieties. Cleavage of the substrate molecule by the proteolytic enzyme results in decreased proximity between X and Y and, correspondingly, in decreased FRET. The progress of the reaction is monitored by observing the decrease in FRET.

A FRET assay to detect conformation change within molecule 1 induced upon interaction with molecule 2, may be configured as follows: A reaction mixture is prepared by combining: (a) molecule 1 labeled at one site with a first conjugate including a fluorochrome X as the detectable group and labeled at another site with a second conjugate including fluorochrome Y as a detectable group, wherein X and Y are able to participate in FRET; and (b) molecule 2. The first and second conjugates can be, for example, of Formula (I) and (II), respectively, and differ in the mean distance and/or mean angle between the pendant phenylarsine moieties. Conformation change within molecule 1 induced upon interaction with molecule 2 results in a change in proximity between X and Y, and, correspondingly, a change in FRET. The progress of the reaction is monitored by observing the change in FRET.

A FRET assay to measure the distance between two sites, 1 and 2, within a molecule of interest, may be configured as follows: the molecule of interest is labeled at site 1 with a first conjugate including fluorochrome X as the detectable group and is labeled at site 2 with a second conjugate including fluorochrome Y as the detectable group, wherein X and Y are able to participate in FRET; fluorescence excitation and emission spectra are collected for X and Y; and the distance, R, is calculated as described supra. The first and second conjugates can be, for example, of Formula (I) and Formula (II), respectively, and differ in the mean distance and/or mean angle between the pendant phenylarsine moieties.

Fluorescence emission intensity, lifetime, polarization, aniosotropy and FRET are further described in the following references: Brand, L. and Johnson, M. L., Eds., *Fluorescence Spectroscopy (Methods in Enzymology, Volume 278)*, Academic Press (1997), Cantor, C. R. and Schimmel, P. R., *Biophysical Chemistry Part 2*, W.H. Freeman (1980) pp. 433-465. Dewey, T. G., Ed., *Biophysical and Biochemical Aspects of Fluorescence Spectroscopy*, Plenum Publishing (1991). Guilbault, G. G., Ed., *Practical Fluorescence, Second Edition*, Marcel Dekker (1990). Lakowicz, J. R., Ed., *Topics in Fluorescence Spectroscopy: Techniques (Volume 1, 1991); Principles (Volume 2, 1991); Biochemical Appli-* cations (*Volume* 3, 1992); *Probe Design and Chemical Sensing* (*Volume* 4, 1994); *Nonlinear and Two-Photon Induced Fluorescence* (*Volume* 5, 1997); *Protein Fluorescence* (*Volume* 6, 2000), Plenum Publishing.

Fluorescence imaging using epi-illumination, confocal, or total-internal-reflection optical microscopy permits characterization of the quantities, locations, and interactions of fluorochrome-labeled target materials within living cells. All fluorescence observables that can be analyzed in vitro—emission intensity, emission lifetime, fluorescence correlation, FP/FA, and FRET—also can be analyzed in living cells (See Nakanishi et al. *Anal. Chem.* 73:2920-2928 (2001); Maiti, S. et al. *Proc. Natl. Acad. Sci. USA* 94: 11753-11757 (1997); Eigen and Rigler, *Proc. Natl. Acad. Sci. USA* 91:5740-5747 (1994) for example of uses of fluorescence in living cells).

The bis-phenylarsine derivatives may be used to label target-sequence-containing molecules within living cells. The bis-phenylarsine derivatives may be introduced into cells by diffusion (for bis-phenylarsine derivatives capable of traversing biological membranes) or by microinjection, electroporation, or vesicle fusion (for any bis-phenylarsine derivative). The target-sequence-containing molecules may be introduced into cells by microinjection, electroporation, or vesicle fusion, or by expression of recombinant genes in situ.

In one especially preferred embodiment, target-sequence-containing protein produced by expression of a recombinant gene within living cells is contacted with the bis-phenylarsine derivatives described herein by incubating cells in medium containing the bis-phenylarsine derivatives. Following labeling, and optionally following further manipulations, the cells are imaged using an epi-illumination, confocal, or total-internal-reflection optical microscope with an optical detector, such as a CCD camera, an intensified CCD camera, a photodiode, or a photomultiplier tube, and fluorescence signals are analyzed.

Most or all of the assays above, in vitro or in vivo, can be adapted for high-throughput screening, using formats, equipment, and procedures apparent to persons skilled in the art.

Examples of fluorochromes and chromophores suitable for use in assays above, in conjunction with the molecules of the invention, are presented in Haugland R. P. *Handbook of Fluorescent Probes and Research Chemicals*, Molecular Probes, sixth edition (1996), ISBN 0-9652240-0-7 (Spence, MTZ, ed). Said fluorochromes and chromophores can be incorporated into polypeptides and other molecules of interest by any suitable method, many of which are well known in the art, including, but not limited to, chemical synthesis, enzymatic synthesis, ribosomal synthesis, chemical ligation, chemical modification, and hapten binding (see Haugland R. P. *Handbook of Fluorescent Probes and Research Chemicals*, supra). Alternatively, fusions of autofluorescent proteins, such as green fluorescent protein, to a polypeptide of interest can be encoded as nucleic-acid fusion constructs, produced in cells, and analyzed in cells or in vitro.

The methods of the invention may be used in many areas of biology and biological research including drug screening, diagnostics and academic research.

It further is contemplated that the at least two different bis-phenylarsine molecules (i.e., the first and second conjugates) can be immobilized on a solid support to allow for immobilization and/or affinity-purification of at least one target material, wherein the target material(s) contain at least two different peptide tags that can bind to the immobilized conjugates in a multi-site-specific fashion.

Immobilization may be accomplished by: (a) covalently attaching the different bis-phenylarsine derivatives to a surface or other solid support (via the detectable group(s) or via a linker); (b) contacting the resulting bis-phenylarsine-derivatives-containing surface or other solid support with a solution including: at least one target material; a first peptide tag bound to the at least one target material; and a second peptide tag bound to the at least one target material; and (c) optionally washing the surface or the solid support to remove unbound material.

Affinity purification may be accomplished by: (a) covalently attaching the different bis-phenylarsine molecules to a surface or other solid support; (b) contacting the resulting bis-phenylarsine-molecules-containing surface or other solid support with a solution including: at least one target material; a first peptide tag bound to the at least one target material; and a second peptide tag bound to the at least one target material; and (c) optionally washing the surface or other solid support to remove unbound material; and (d) eluting the target molecules with a low-molecular-weight monothiol (e.g., β-mercaptoethanol) or, preferably, a low-molecular-weight dithiol (e.g., dithiothreitol or ethanedithiol). The solid support may be, for example, a surface, a bead, a gel, or a chromatographic matrix.

The invention also provides kits. For example, the invention provides a kit that includes: (a) at least one vector including sequence encoding a first peptide tag and/or a second peptide tag; (b) a first conjugate having a detectable group and two pendant phenylarsine moieties comprising a first tag binding group; wherein the first conjugate preferentially associates with the first peptide tag; and (c) a second conjugate having a detectable group and two pendant phenylarsine moieties comprising a second tag binding group; wherein the second conjugate preferentially associates with said second peptide tag. The mean distance and/or mean angle between the pendant phenylarsine moieties in the first conjugate in the kit is different from the mean distance and/or mean angle between the pendant phenylarsine moieties in the second conjugate in the kit. In one embodiment, the first peptide tag is encoded by sequence in a first vector and the second peptide tag is encoded by sequence in a second vector.

The kit can also include a reagent that promotes the formation of a complex between the at least two different bis-phenylarsine molecules and the at least two different peptide tags. In one embodiment, the reagent is a monothiol or a dithiol.

The first and second conjugates (i.e., labels) in the kit can each be represented by the general structural Formula (I) and tautomers, acids and salts thereof, wherein X in Formula (I) is a fluorescent moiety. In one embodiment, the corresponding first and second peptide tags are of the form: $C(X)_iC(X)_jC(X)_kC$, wherein C is cysteine, X is any amino acid, and i, j, and k are each independently selected from 0 or an integer from 1-8.

In a preferred embodiment, the first conjugate in the kit is represented by the general structural Formula (I) and tautomers, acids and salts thereof, wherein X in Formula (I) is a fluorescent moiety; and the second conjugate is represented by the general structural Formula (II) and tautomers, anhydrides and salts thereof, wherein one or more positions of Formula (II) are substituted so as to add a fluorescent moiety. The first peptide tag interacts with the first conjugate, but does not interact substantially with the second conjugate and is of the form: $C(X)_iC(X)_jC(X)_kC$, wherein C is cysteine, X is any amino acid, and i, j, and k are each independently selected from 0 or an integer from 1-8.

Desirably, the second peptide tag for use in combination with the first tag is of the form $C(X)_iC$, wherein X is any amino acid and i is 0-6. Specific examples of suitable tag combinations are the same as those described above.

The invention provides useful peptide tag combinations and target materials or target material sets including these tag combinations. Moreover, the invention provides isolated or recombinant nucleic acids or nucleic acid sets encoding these materials, which can be provided in kits.

For example, the present invention provides a composition including: (i) a peptide sequence of the form: $C(X)_iC(X)_jC(X)_kC$, wherein C is cysteine, X is any amino acid, and i, j, and k are each independently selected from 0 or an integer from 1-8; and (ii) a peptide sequence of the form $C(X)_iC$, wherein X is any amino acid and i is 0-6. Specific examples of suitable tag combinations are the same as those described above.

Further provided herein is a composition that includes: (i) at least one target material; (ii) a first peptide tag bound to the at least one target material and being of the form: $C(X)_iC(X)_jC(X)_kC$, wherein C is cysteine, X is any amino acid, and i, j, and k are each independently selected from 0 or an integer from 1-8; (iii) a second peptide tag bound to the at least one target material and being of the form $C(X)_iC$, wherein X is any amino acid and i is 0-6. The at least one target material can be a polypeptide or a set of polypeptides. Specific examples of suitable tag combinations are the same as those described above.

The invention also provides a composition including: (i) a first nucleic acid sequence encoding a first peptide tag of the form: $C(X)_iC(X)_jC(X)_kC$, wherein C is cysteine, X is any amino acid, and i, j, and k are each independently selected from 0 or an integer from 1-8; and (ii) a second nucleic acid sequence encoding a second peptide tag of the form $C(X)_iC$, wherein X is any amino acid and i is 0-6. This composition can be included within a kit according to the present invention. The first and second nucleic acid sequences can be provided on the same or different vectors within the kit, for example. Specific examples of suitable tag combinations which can be encoded by the nucleic acids or nucleic acid sets are the same as those described above.

Moreover, the invention provides a composition including an isolated or recombinant nucleic acid or nucleic acid set encoding: (i) at least one target material; (ii) a first peptide tag bound to the at least one target material and being of the form: $C(X)_iC(X)_jC(X)_kC$, wherein C is cysteine, X is any amino acid, and i, j, and k are each independently selected from 0 or an integer from 1-8; and (iii) a second peptide tag bound to the at least one target material and being of the form $C(X)_iC$, wherein X is any amino acid and i is 0-6. The at least one target material can be a polypeptide or a set of polypeptides. Moreover, this composition can be provided in a kit according to the present invention. For example, a vector or set of vectors encoding components (i), (ii) and (iii) can be provided in kit form. Specific examples of suitable tag combinations which can be encoded by these nucleic acids or nucleic acid sets are the same as those described above.

It will be apparent that the present invention has been described herein with reference to certain preferred or exemplary embodiments. The preferred or exemplary embodiments described herein may be modified, changed, added to, or deviated from without departing from the intent, spirit and scope of the present invention, and it is intended that all such additions, modifications, amendments and/or deviations be included within the scope of the following claims.

The following references are herein incorporated by reference and relate to the examples set forth below:

1. Fisher, N. and Hamer, F., Tricarbocyanines. *J. Chem. Soc.* 189-193 (1933).
2. Mujumdar, et al., R., "Cyanine dye labeling reagents: sulfoindocyanine succinimidyl esters," *Bioconj. Chem.* 4, 105-111 (1993).
3. Mekler, M., et al., "Structural organization of RNA polymerase holoenzyme and the RNA polymerase-promoter open complex: systematic fluorescence resonance energy transfer and distance-constrained docking," *Cell*, 108, 599-614 (2002).
4. Niu, W., "Identification and characterization of interactions between a transcription activator and the transcription machinery," Ph.D dissertation, Rutgers University, New Brunswick, N.J. (1999).
5. Tang, H., et al., "Location, structure, and function of the target of a transcriptional activator protein," *Genes & Dev*, 8:3058-3067 (1995).
6. Kunkel, T. "Rapid and efficient site-specific mutagenesis without phenotypic selection," *Proc. Natl. Acad. Sci. USA* 82, 488-492 (1985).
7. Tang, H., et al., "Rapid RNA polymerase genetics: one-day, no-column preparation of reconstituted recombinant *Escherichia coli* RNA polymerase," *Proc. Natl. Acad. Sci. USA* 92, 4902-4906 (1995).
8. Studier, F., et al., "Use of T7 RNA polymerase to direct expression of cloned genes,: *Methods Enzylomol.* 185, 125-138 (1990).

EXAMPLE 1

Synthesis of Cy3 bis-propionamido-phenylarsineoxide [Cy3-(PAO)$_2$]

1.1: 4-(bromopropionamido)-phenylarsineoxide

Bromopropionic acid anhydride [formed by reacting bromopropionic acid (1.66 g, 10.86 mmol) with DCC (1.12 g, 5.43 mmol) in 20 ml anhydrous dichloromethane for 15 minutes at 25° C., and filtering off the solid that precipitated] was added to a solution of aminophenylarsineoxide (1 g, 5.43 mmol, synthesized according to published protocol) in 10 ml DMF, and allowed to stir overnight. The amino phenylarsineoxide was rendered soluble by adding to it 10.86 mmol HCl/ether followed by neutralization with triethylamine and filtering the away the solid that formed. The solution was quenched with 20 ml water, and filtered to remove solids. The filtrate was evaporated to an oil, and purified via flash chromatography. In later preparations, 3-bromopropionyl chloride was used instead of the anhydride.

Alternative Preparation:

4-(bromopropionanido)-phenylarsanilic acid

Into 20 ml water was added potassium hydroxide (1 g, 18.4 mmol), p-arsanilic acid (2.04 g, 9.4 mmol), and sodium bicarbonate (3.06 g, 28 mmol). The suspension was stirred until all the solids dissolved. Ice was added to the solution until some ice remained in the solution. Into the icy solution was added 3-bromopropionyl chloride (2.38 g, 13.9 mmol) aliquot-wise over 2 minutes. The solution was vigorously stirred for 5 minutes, then extracted with 10 ml dichloromethane in a separatory funnel. The dichloromethane layer was discarded, the aqueous layer was cooled on ice, and acidified with 50% sulfuric acid until the pH was 1. A white solid precipitated, and was collected via vacuum filtration. Yield: 2.967 g (8.4 mmol, 89% yield). (M+H$^+$): expected, 352, 354; found, 352, 354.

4-(bromopropionamido)-phenylarsineoxide 20 mg of sodium iodide was added to a solution of 4-(bromopropionamido)-phenylarsanilic acid (1 g, 2.84 mmol) in 10 ml methanol and 10 ml 48% hydrobromic acid. Sulfur dioxide was bubbled into the stirred solution for 15 minutes, during which time a white solid precipitated. The gas was removed, and the suspension stirred for another 5 minutes. The solid was collected via vacuum filtration. Yield: 0.75 g, 2.23 mmol, 78% yield.

1.2: 4-(2,33-trimethylindolyl)-propionaniido-phenylarsineoxide 4-(Bromopropionamido)-phenylarsineoxide (Example 1.1; 0.23 g, 0.72 mmol) and 2,3,3-trimethylindolenine (Aldrich; 160 mg, 10 mmol) were mixed and heated at 80° C. in a screw-top vial for 6 hours. Upon cooling, the purple mass was triturated with copious diethyl ether. The crude product was used without further purification.

1.3: Cy3 bis-propionamido-phenylarsineoxide [Cy3-(PAO)$_2$]

To 4-(2,33-trimethylindolyl)-propionamido phenylarsineoxide (Example 1.2; 0.72 mmol) was added triethyl orthoformate (Aldrich; 100 µl, 0.68 mmol) and 500 µl pyridine in a screw-cap vial. The mixture was heated at 80° C. for 6 h. Upon cooling, the mixture was triturated with a copious amount of diethyl ether. The solid was collected and purified via flash chromatography (silica, 240-400 mesh, 1-20% MeOH—CHCl$_3$.). Yield: 63 mg. (M+H$^+$): expected, 839.7; found, 839.4. The mass spectrum indicated that the compound was mainly in the arsonous form. Absorbance at 550 nm and 260 nm indicate the presence of the Cy3 moiety and the phenylarsine group.

EXAMPLE 2

Synthesis of Cy5 bis-propionamido-phenylarsineoxide [Cy5-(PAO)$_2$]

2.1: Cy5 bis-propionamido-phenylarsineoxide [Cy5-(PAO)$_2$]

Into 4-(2,33-trimethylindolyl)-propionamido-phenylarsineoxide (Example 1.2; crude 130 mg, 0.26 mmol) was added 1,3,3-trimethoxypropene (Karl Industries, Inc.; 50 µl, 0.38 mmol) in 400 µl pyridine in a screw-cap vial. The reaction was heated with a heat gun for 3 min, until a turquoise color imparted. Upon cooling, the reaction mixture was triturated with diethyl ether and ethyl acetate. The solid was collected and purified via flash chromatography (silica, 240-400 mesh, 1-20% MeOH—CHCl$_3$.). Yield: 3 mg. M+H$^+$ (after dissolution in methanol in the presence of trace acetic acid): expected, 865.7; found, 921.3 (arsonous methyl ether).

EXAMPLE 3

Synthesis of Cy3 bis-propionamido-phenylarsine-ethanedithiol [Cy3-(PAEDT)$_2$], method A 3.1: 4-(bromopropionamido)-phenylarsine-EDT 1,2-Ethanedithiol (Aldrich; 25 µl, 0.30 mmol) was added to 4-(bromopropionamido)-phenylarsineoxide (Example 1.1; 100 mg, 0.30 mol) dissolved in 1 ml of hot methanol. After 5 min, a white solid precipitated and was collected. Yield: 63.7 mg, 0.16 mmol, 53%.

3.2: 4-(2,3,3-trimethylindolyl)-propionamido-phenylarsine-EDT 4-(Bromopropionamido)-phenylarsine-EDT (Example 3.1; 34 mg, 0.086 mmol) and 2,3,3-trimethylindolenine (Aldrich; 50 mg, 0.3 mmol) and were mixed and heated at 90° C. in a screw-top vial for 6 hours. Upon cooling, the purple mass was triturated with copious diethyl ether. Yield: 40 mg. The crude product was used without further purification.

3.3: Cy3 bis-propionamido-phenylarsine-ethanedithiol [Cy3-(PAEDT)$_2$]

4-(2,33-trimethylindolyl)-propionamido-phenylarsine-EDT (crude, 19 mg, 0.034 mmol) was suspended in 200 µl pyridine and triethyl orthoformate (50 µl, 0.34 mmol) in a screw cap glass vial. The mixture was heated with a heat gun until the deep violet color of the dye stayed constant. Upon cooling to room temperature, the pyridine was evaporated to yield a deep purple solid. It was dissolved in 1 ml methanol and precipitated with ether to yield 23 mg of crude product. FIG. 1, method A depicts the method of synthesis of Cy3-(PAEDT)$_2$.

EXAMPLE 4

Synthesis of Cy3 bis-propionamido-phenylarsine-ethanedithiol [Cy3-(PAEDT)$_2$], method B 4.1: Cy3 bis-propionamido-phenylarsine-ethanedithiol [Cy3-(PAEDT)$_2$]

Into a solution of Cy3-(PAO)$_2$ (Example 1.3; 300 mmol in 100 µl DMF), was added 1 µl 1,2-ethanedithiol (Aldrich, 12 µmol). After 10 min at room temperature, the sample was evaporated under high vacuum (yielding an oil), dissolved in chloroform, and purified via flash chromatography (silica, 240400 mesh, 1-20% MeOH—CHCl$_3$.). Yield: 220 nmol, 73%. (M+H$^+$): expected, 955.2; found, 955.4. FIG. 1, method B depicts this method of synthesis of Cy3-(PAEDT)$_2$.

EXAMPLE 5

Synthesis of Cy5 bis-propionamido-phenylarsine-ethanedithiol [Cy5-(PAEDT)$_2$], method A 5.1: Cy5 bis-propionamido-phenylarsine-ethanedithiol; Cy5-(PAEDT)$_2$ 4-(2,33-trimethylindolyl)-propionamido-phenylarsine-EDT (crude, 17 mg, 0.031 mmol) was suspended in 200 µl pyridine and 1,3,3-trimethoxypropene (50 µl, 0.38 mm01) in a screw cap glass vial. The mixture was heated with a heat gun until the deep blue color of the dye stayed constant. Upon cooling to room temperature, the pyridine was evaporated to yield a deep blue solid. It was redissolved in 1 ml chloroform and purified using silica chromatography (straight chloroform followed by gradual increase of methanol to 10% methanol). Yield: 7.26 mg, 8.15 µmol, 54%. (M+H$^+$): expected, 981.13; found, 981.3. FIG. 1, method A depicts this method of synthesis of Cy5-(PAEDT)$_2$.

EXAMPLE 6

Synthesis of Cy5
bis-propionamido-phenylarsine-ethanedithiol
[Cy5-(PAEDT)$_2$], method B 6.1: Cy5 bis-propionamido-phenylarsine-ethanedithiol; Cy5-(PAEDT)$_2$ Into a solution of Cy5-(PAO)$_2$ (Example 1.3; 300 nmol in 100 µl DMF), was added 1 µl 1,2-ethanedithiol (Aldrich, 12 µmol). After 10 min at room temperature, the sample was evaporated under high vacuum (yielding an oil), dissolved in chloroform, and purified via flash chromatography (silica, 240-400 mesh, 1-20% MeOH—CHCl$_3$.). Yield: 108 nmol, 36%. (M+H$^+$): expected, 981.13; found, 981.3. FIG. 1, method B depicts this method of synthesis of Cy5-(PAEDT)$_2$

EXAMPLE 7

Synthesis of Cy7
bis-propionamido-phenylarsine-ethanedithiol
[Cy7-(PAEDT)$_2$]

7.1: Cy7 bis-propionamido-phenylarsine-ethanedithiol; Cy7-(PAEDT)$_2$

Into 4-(2,3,3-trimethylindolyl)-propionamido-phenylarsine-EDT (Example 3.1; 5.5 mg, 10 µmol) was added glutacoldnadehyde dianil HCl (5.68 mg, 20 µmol, synthesized according to Fisher, N. and Hamer, F. "Tricarbocyanines," *J. Chem. Soc.* 189-193 (1933)) in 50 µl pyridine in a screw-cap vial. The reaction mixture was heated with a heat gun for 3 min until a dark blue color appeared. Upon cooling, the reaction mixture was triturated with diethyl ether, dissolved in the smallest volume MeOH and again triturated with diethyl ether. The solid was collected and purified via flash chromatography (silica, 240-400 mesh, 1-10% MeOH—CHCl$_3$.). The slowest green fraction was collected and gave the correct UV-VIS absorbance (270 nm for the phenylarsine-ethanedithiol moiety and 765 nm for Cy7). Yield: 0.16 µmol (3.2%). (M+H$^+$): expected, 1007.2; found, 1007.2.

EXAMPLE 8

Synthesis of Cy3 bis-sulfonato
bis-propionamido-phenylarsine-ethanedithiol
[sulfo-Cy3-(PAEDT)$_2$]

8.1: 4-(2,3,3-trimethylindolyl-5-sulfonato)-propionamido-phenylarsine-ethanedithiol 4-(Bromopropionamido)-$_{phenylarsine}$-EDT (Example 3.1; 50 mg, 0.127 mmol) and the potassium salt of 2,3,3-trimethyl-indoleninium-5-sulfonate (30 mg, 10.8 mmol; synthesized according to Mujumdar, et al., "Cyanine dye labeling reagents: sulfoindocyanine succinimidyl esters," *Bioconj. Chem.* 4, 105-111 (1993)) were suspended in 500 µl dichlorobenzene and heated at 90° C. in a screw-top vial for 6 hours. Upon cooling, the dichlorobenzene was decanted, the solid was triturated with copious diethyl ether, redissolved in the smallest volume of hot methanol, and upon cooling, reprecipitated with ether. Yield: 50 mg. The crude product was used without further purification.

8.2: Cy3 bis-sulfonato bis-propionamido-phenylarsine-ethanedithiol; [sulfo-Cy3-(PAEDT)$_2$]

To 4-(2,3,3-trimethyl-5-sulfoindolyl)-propionamido-phenylarsine-EDT (Example 8.1; crude, 50 mg) was added 200 µl pyridine and triethyl orthoformate (100 µl, 0.67 mmol) in a screw cap glass vial. The mixture was heated with a heat gun until the deep purple color of the dye stayed constant. Upon cooling to room temperature, the pyridine was evaporated to yield a deep purple solid, which was triturated with ether. About 25% of the crude solid was purified by reverse-phase C18 HPLC, and the main peak collected. Yield: 1 mg. (M$^-$): expected, 1114.12; found, 1114.1.

EXAMPLE 9

Synthesis of Cy5 bis-sulfonato
bis-propionamido-phenylarsine-ethanedithiol
[sulfo-Cy5-(PAEDT)$_2$]

9.1: Cy5 bis-sulfonato bis-propionamido-phenylarsine-ethanedithiol; [sulfo-Cy5-(PAEDT)$_2$]

To 4-(2,3,3-trimethyl-5-sulfoindolyl)-propionamido-phenylarsine-EDT (Example 8.1; crude, 12 mg) was added 100 µl pyridine and 1,3,3-trimethoxypropene (25 µl, 0.19 mmol) in a screw cap glass vial. The mixture was heated with a heat gun until the deep blue color of the dye stayed constant. Upon cooling to room temperature, the pyridine was evaporated to yield a deep blue solid. The solid was triturated with ether to give 20 mg of a deep blue solid.

EXAMPLE 9A

Synthesis of Cy7 bis-sulfonato
bis-propionamido-phenylarsine-ethanedithiol
[Cy7-(SO3)$_2$-(PAEDT)$_2$]

9A.1: Cy7 bis-sulfonato bis-propionamido-phenylarsine-ethanedithiol; [Cy7-(SO3)$_2$-(PAEDT)$_2$]

Glutaconaldehyde dianil hydrochloride (3.6 mg, 12.5 µmol) was heated in DMF (300 µl), acetic anhydride (20 µl) and pyridine (15 µl) in a small capped-vial till the solution turned colorless. The hot solution was added to 4-(2,3,3-trimethyl-5-sulfoindolyl)-propionamido-phenylarsine-EDT (Example 8.1; cleaned by triturating with methanol till supernatant was clear, 15 mg, 25 µmol) and further heated until the suspension obtained a deep green color. The reaction mixture was evaporated to dryness, and the solid was triturated copiously with methanol. The solid was dissolved in 20% DMF and purified on a semi-prep C18 reverse phase column. Yield: 234 nmol, (M$^-$): expected, 1166.2; found, 1166.5.

EXAMPLE 10

Synthesis of Cy3 bis-sulfonato bis-propionamido-
phenylarsine-propanedithiol-sulfonic acid [sulfo-
Cy3-(PAsulfoPDT)$_2$]

10.1: Cy3 bis-sulfonato bis-propionamido-phenylarsine-propanedithiol-sulfonic acid [sulfo-Cy3-(PAsulfoPDT)$_2$]

To sulfo-Cy3-(PAEDT)$_2$ (Example 8.2; 500 nmol in 1 ml DMF) was added 2,3-dimercapto-1-propanesulfonic acid, sodium salt (20 µM in 0.5 ml MeOH). The reaction was allowed to proceed for 1 hour at room temperature, after which solvent was evaporated under high vacuum. The sample was re-dissolved in 2 ml water and desalted using two Sep-Pak C18 cartridges, evaporated, and purified using reversed-phase HPLC on C18. Yield: 500 nmol.

EXAMPLE 11

Synthesis of Cy5 bis-sulfonato bis-propionamido-phenylarsine-propanedithiol-sulfonic acid [sulfoCy5-(SO3)$_2$—(PAsulfoPDT)$_2$]

11.1: Cy5 bis-sulfonato bis-propionamido-phenylarsine-propanedithiol-sulfonic acid [sulfo-Cy5-(PAsulfoPDT)$_2$]

To sulfo-Cy5-(PAEDT)$_2$ (Example 9.1; 400 nmol in 1 ml DMF) was added 2,3-dimercapto-1-propanesulfonic acid, sodium salt (20 µM in 0.5 ml MeOH). The reaction was allowed to proceed for 1 hour at room temperature, after which solvent wqs evaporated under high vacuum. The sample was re-dissolved in 2 ml water and desalted using two Sep-pak C18 cartridges, evaporated, and purified using reversed-phase HPLC on C18. Yield: 300 nmole (M$^{2-}$): expected, 663.5; found, 663, 664, 665.

Table 1 depicts the spectroscopic properties of fluorochrome conjugates described above in methanol. The excitation and emission maxima are listed.

TABLE 1

Spectroscopic Properties of Fluorochrome Conjugates in Methanol

| fluorochrome | $\lambda_{max,exc}$ (nm) | $\lambda_{max,em}$ (nm) |
|---|---|---|
| Cy3-(PAO)$_2$ | 552 | 566 |
| Cy3-(PAEDT)$_2$ | 552 | 567 |
| sulfo-Cy3-(PAEDT)$_2$ | 558 | 572 |
| sulfo-Cy3-(PAsulfoPDT)$_2$ | 557 | 570 |
| Cy5-(PAO)$_2$ | 647 | 665 |
| Cy5-(PAEDT)$_2$ | 648 | 666 |
| sulfo-Cy5-(PAEDT)$_2$ | 650 | 673 |
| sulfo-Cy5-(PAsulfoPDT)$_2$ | 652 | 667 |
| Cy7-(PAEDT)$_2$ | 743 | 774 |

EXAMPLE 12

Site-Specific Labeling 12.1: Plasmids Encoding Untagged and Tagged α Derivatives Plasmid pHTf1α-Bam encodes *Escherichia coli* RNA polymerase α subunit under control of the lpp-'lacPUV5 tandem promoter (Mekler et al., *Cell*, 108, 599-614 (2002); Niu, W., Ph.D dissertation, Rutgers University, New Brunswick, N.J. (1999); Tang et al., *Genes & Dev*, 8:3058-3067 (1995)). The following plasmids encoding tetracysteine-tagged α derivatives were constructed by use of site-directed mutagenesis (methods as in Kunkel, *Proc. Natl. Acad. Sci. USA* 82, 488-492 (1985)):

pHTf1α-Bam(CGPCN), encodes α-CGPCN
pHTf1α-Bam(CGPCCGPCN), encodes α-CGPCCGPCN
pHTf1α-Bam(CGPCGCGPCN), encodes α-CGPCGCGPCN
pHTf1α-Bam(CGPCGGCGPCN), encodes α-CGPCGGCGPCN
pHTf1α-Bam(CPGCN), encodes α-CPGCN
pHTf1α-Bam(CPGCCPGCN), encodes α-CPGCCPGCN
pHTf1α-Bam(CPGCGCPGCN), encodes α-CPGCGCPGCN
pHTf1α-Bam(CPGCGGCPGCN), encodes α-CPGCGGCPGCN
pHTf1α-Bam(CCGPCCN), encodes α-CCGPCCN
pHTf1α-Bam(CCGPCCN), encodes α-CCGPCCN
pHTf1α-Bam(CCPGPCCN), encodes α-CCPGPCCN
pHTf1α-Bam(CCGPGCCN), encodes α-CCGPGCCN
pHTf1α-Bam(CCPGPGCCN), encodes α-CCPGPGCCN
pHTf1α-Bam(CCGPGPCCN), encodes α-CCGPGPCCN Plasmid pHTT7f1-NHα encodes *Escherichia coli* RNA polymerase α subunit with an N-terminal hexahistidine tag under control of the bacteriophage T7 gene 10 promoter (Tang et al., *Proc. Natl. Acad. Sci. USA* 92, 49024906 (1995)). pHTT7f1-NHα derivatives were constructed by replacing the ClaI-BamHI rpoA segment of plasmid pHTf1T7-NHα with corresponding segments of plasmid pHTf1α-Bam derivatives.

12.2: Labeling of Untagged and Tagged α Derivatives, Crude Cell Lysates

Transformants of *E. coli* strain BL21(DE3) (Novagen; Studier et al., *Methods Enzylomol.* 185, 125-138 (1990)) with pHTT7f1-NHα derivatives were shaken at 37° C. in 10 ml LB containing 2 mg/ml ampicillin until OD$_{600}$=0.7, induced by addition of IPTG to 1 mM, and further shaken for another 3 h at 37° C. Cells were harvested by centrifugation (4,600×g; 5 min, 4° C.), and stored at −80° C. Immediately before use, cells were re-suspended in 600 µl 100 mM Tris-HCl, pH 7.9, 200 mM NaCl, 1 mM β-mercaptoethanol, 1 mM phenylmethylsulfonyl fluoride, 7 µM pepstatin A, and 23 µg/ml lysozyme, incubated 5 min at 4° C., and lysed by sonication. Lysates were cleared by centrifugation (16,000× g; 5 min at 4° C.).

To 100 µl cleared lysate, was added 0, 1, or 10 µl 0.5 M dithiothreitol (DTT), and bis-arsenical Cy3-(PAO)$_2$, Cy3-(PAEDT)$_2$, Cy5-(PAO)$_2$, or Cy5-(PAEDT)$_2$ to 20 µM (added as 2 µl of 1 mM solution in dimethylformamide). Following 20 min at 25° C., 15 µl aliquots were mixed with 5 µl 0.25 M Tris-HCl, pH 6.8, 2% SDS, 0.01% bromophenol blue, and 30% glycerol and analyzed by SDS-PAGE on 4-20% gradient gels (Criterion, Bio-Rad, Inc.), followed by x/y fluorescence scanning (for Cy3: Molecular Dynamics FluorImager 595, with excitation=514 nm and emission>610 nm; for Cy5: Molecular Dynamics Storm 860, with excitation=635 nm and emission>650 nm).

Labeling of tagged α derivatives was specific; thus, in reactions in the presence of 5 mM DTT, fewer than ten other proteins in the cell lysates were labeled detectably, and, in reactions in the presence of 50 mM DTT, only one other protein in the cell lysate was labeled detectably. Labeling of tagged α derivatives was tag-dependent and required specific tetracysteine tags; thus, in reactions in the presence of 5 mM or 50 mM DTT, labeling was observed with α-CCGPCCN, α-CCGPCCN, αCCPGPCCN, α-CCGPGCCN, α-CCPGPGCCN, and α-CCGPGPCCN and, to a lesser degree, α-CGPCCGPCN, but no labeling was observed with untagged α, α-CGPCN and α-CPGCN.

12.3: Labeling of Tagged α, Purified Protein

To cleared lysates (1.4 ml prepared as above, but from 50 ml cultures), was added 2.8 µl 1 M imidazole and 0.2 ml Ni$^{2+}$-NTA agarose (Qiagen). Following 15 min at 25° C., samples were transferred to 2 ml columns (Poly-Prep, Bio-Rad, Inc.), washed with 10 ml buffer A (100 mM Tris-HCl, pH 7.9, 200 mM NaCl, 2 mM imidazole, and 5% glycerol), washed with 2 ml buffer A containing 10 mM imidazole, and eluted with 2×1 ml buffer A containing 40 mM imidazole. Samples were dialyzed against 100 mM Tris-HCl, pH 7.9, 200 mM NaCl, 1 mM β-mercaptoethanol, 1 mM DTT, and 5% glycerol. Yield: ~300 µg. Purity:~~85%.

Labeling reactions contained (11 µl): 10 µM α derivative, 450 µM bis-arsenical Cy3-(PAO)$_2$, Cy3-(PAEDT)$_2$, Cy5-(PAO)$_2$, or Cy5-(PAEDT)$_2$, 100 mM Tris-HCl, pH 7.9, 200 mM NaCl, 0.5, 5, or 50 mM DTT, 1 mM β-mercaptoethanol, 9% dimethyformamide, and 5% glycerol. Following 20 min at 25° C., 15 μl aliquots were mixed with 5 μl 10.25 M Tris-HCl, pH 6.8, 2% SDS, 0.01% bromophenol blue, and 30% glycerol and analyzed by SDS-PAGE as described in Example 12.2.

Labeling was tag-dependent; thus, in reactions in the presence of 0.5 mM or 5 mM DTT, labeling was observed with α-CCPGCCN, but no labeling was observed with untagged α.

EXAMPLE 13

Immobilization/Affinity-Chromatography 13.1: Immobilization/Affinity-Chromatography of Untagged and Tagged α Derivatives Cleared lysates (1 ml, prepared as described above, but from 20 ml cultures) were equilibrated with 1 ml phenylarsine oxide agarose (Thiobond resin; Invitrogen, Inc.; re-suspended and charged per manufacturer's procedures) for 30 min at 25° C. with gentle rocking. Samples were transferred to disposable columns (Poly-Prep, Bio-Rad, Inc.), washed with 3×2 ml buffer B (100 mM Tris-HCl, pH 7.9, 200 mM NaCl, 1 mM EDTA, 1 mM β-mercaptoethanol, and 5% glycerol), washed with 3×2 ml buffer B containing 0.5 mM DTT, washed with 3×2 ml buffer B containing 5 mM DTT, and eluted with 3×2 ml buffer B containing 50 mM DTT. Aliquots (20 μl) were analyzed by SDS-PAGE as described in Example 12.2.

Tagged α could be immobilized on phenylarsine oxide agarose in the absence of DTT, could be retained in the presence of 0.5 mM DTT and could be eluted in the presence of 5 and 50 mM DTT resulting in ~10-fold purification (α-CCGPCCN and α-CCPGCCN; yield, ~200 μg; purity, >95%). Immobilization and retention was specific; thus, fewer than ten other proteins in the cell lysates were detectably immobilized and retained in the presence of 5 mM DTT. Immobilization was tag-dependent; thus, untagged a could not be retained in the presence of 5 mM DTT.

EXAMPLE 14

Tagged Peptides 14.1: Synthesis of Tagged Peptides

The following tetracysteine-tagged peptides were synthesized and HPLC-purified. Peptides were synthesized in three sets: set A (one tetracysteine tag, charge=0), set B (two tetracysteine tags, charge =−1) and set C (two tetracysteine tags):

Set A: (one tetracysteine tag, charge=0)
Ac—WNCCCCN—CONH$_2$ ("0$^{0''}$")
Ac—WNCCGCCN—CONH$_2$ ("G1$^{0''}$")
Ac—WNCCGGCCN—CONH$_2$ ("G2$^{0''}$")
Ac—WNCCGGGCCN—CONH$_2$ ("G3$^{0''}$")
Ac—WNCCGGGGCCN—CONH$_2$ ("G4$^{0''}$")
Ac—WNCCGPCCN—CONH$_2$ ("GP$^{0''}$")
Ac—WNCCGPGCCN—CONH$_2$ ("GPG$^{0''}$")
Ac—WNCCPGCCN—CONH$_2$ ("PG$^{0''}$")
Ac—WNCCPGPCCN—CONH$_2$ ("PGP$^{0''}$")
Ac—WNCGCCGCN—CONH$_2$
Ac—WNCGCGCGCN—CONH$_2$
Ac—WNCGGCCGGCN—CONH$_2$
Ac—WNCGPCCGPCN—CONH$_2$
Ac—WNCPGCCPGCN—CONH$_2$
Ac—WNCGPCGCGPCN—CONH$_2$
Ac—WNCPGCGGCPGCN—CONH$_2$ Ac—WNCGPCGGCGPCN—CONH$_2$
Ac—WNCPGCGGCPGCN—CONH$_2$
Set B: (one tetracysteine tag, charge=−1)
Ac-EWNCCCCN—CONH$_2$ ("0")
Ac-EWNCCGCCN—CONH$_2$ ("G1")
Ac-EWNCCGGCCN—CONH$_2$ ("G2")
Ac-EWNCCGGGCCN—CONH$_2$ ("G3")
Ac-EWNCCGGGGCCN—CONH$_2$ ("G4")
Ac-EWNCCPCCN—CONH$_2$ ("P1")
Ac-EWNCCPPCCN—CONH$_2$ ("P2")
Ac-EWNCCPPPCCN—CONH$_2$ ("P3")
Ac-EWNCCPPPPCCN—CONH$_2$ ("P4")
Ac-EWNCCPPPPPCCN—CONH$_2$ ("P5")
Ac-EWNCCPPPPPPCCN—CONH$_2$ ("P6")
Ac-EWNCCGPCCN—CONH$_2$ ("GP")
Ac-EWNCCGPGCCN—CONH$_2$ ("GPG")
Ac-EWNCCGPPGCCN—CONH$_2$ ("GP2G")
Ac-EWNCCGPPPGCCN—CONH$_2$ ("GP3G")
Ac-EWNCCGPPPPGCCN—CONH$_2$ ("GP4G")
Ac-EWNCCGPPPPPGCCN—CONH$_2$ ("GP5G")
Ac-EWNCCGPPPPPPGCCN—CONH$_2$ ("GP6G")
Ac-EWNCCPGCCN—CONH$_2$ ("PG")
Ac-EWNCCPGPCCN—CONH$_2$ ("PGP")
Ac-EWNCCPPGPPCCN—CONH$_2$ ("P2GP2")
Ac-EWNCCPPPGPPPCCN—CONH$_2$ ("P3GP3")
Set C: (two tetracysteine tags)
Ac-EWNCCPPPCCN—PPPPPPPPP—NCCGCCN—CONH$_2$ ("SARP-P3/G1-PP9")
Ac-EWNCCPPPCCN—PPPPPPPPPPPP—NCCGCCN—CONH$_2$ ("SARP-P3/G1-PP12")
Ac-EWNCCPPPCCN-AE-AAAKEAAAKEAAAKEAAAKA-NCCGCCN—CONH$_2$ ("SARP—P3/G1-HL4X")
Ac-EWNCCPPPPCCN—PPPPPPPPP—NCCGCCN—CONH$_2$ ("SARP-P4/G1-PP9")
Ac-EWNCCPPPPCCN—PPPPPPPPPPPP—NCCGCCN—CONH$_2$ ("SARP-P4/G1-PP12")
Ac-EWNCCPPPPCCN-AE-AAAKEAAAKEAAAKEAAAKA-NCCGCCN—CONH$_2$ ("SARP—P4/G1-HL4X")

EXAMPLE 15

Tagged Proteins 15.1: Plasmids

Plasmid pHTT7f1-NHα encodes *Escherichia coli* RNA polymerase α subunit with an N-terminal hexahistidine tag under control of the bacteriophage T7 gene 10 promoter (Studier, et al. (1990) Methods Eznymol. 185, 125-138). The following pHTT7f1-NHα derivatives were constructed by use of site-directed mutagenesis (methods as in Tang, et al. (1995) Genes Dev. 8, 3058-3067):

pHTT7f1-NHα(CCCCN), encodes α-CCCCN ("α-0")
pHTT7f1-NHα(CCGCCN), encodes α-CCGCCN ("α-G1")
pHTT7f1-NHα(CCGGCCN), encodes α-CCGGCCN ("α-G2")
pHTT7f1-NHα(CCGGGCCN), encodes α-CCGGGCCN ("α-G3")
pHTT7f1-NHα(CCGGGGCCN), encodes α-CCGGGGCCN ("α-G4")
pHTT7f1-NHα(CCPCCN), encodes α-CCPCCN ("α-P1")
pHTT7f1-NHα(CCPPCCN), encodes α-CCPPCCN ("α-P2")
pHTT7f1-NHα(CCPPPCCN), encodes α-CCPPPCCN ("α-P3")

pHTT7f1-NHα(CCPPPPCCN), encodes α-CCPPPPCCN ("α-P4")

pHTT7f1-NHα(CCPPPPPCCN), encodes α-CCPPPP-PCCN ("α-P5")

pHTT7f1-NHα(CCPPPPPPCCN), encodes α-CCPPPPP-PCCN ("α-P6")

pHTT7f1-NHα(CGPCN), encodes α-CGPCN pHTT7f1-NHα(CGPCCGPCN), encodes α-CGPCCGPCN pHTT7f1-NHα(CGPCGCGPCN), encodes α-CGPCGCG-PCN pHTT7f1-NHα(CGPCGGCGPCN), encodes α-CGPCG-GCGPCN pHTT7f1-NHα(CPGCN), encodes α-CPGCN pHTT7f1-NHα(CPGCCPGCN), encodes α-CPGCCPGCN pHTT7f1-NHα(CPGCGCPGCN), encodes α-CPGCGCPGCN pHTT7f1-NHα(CPGCGGCPGCN), encodes α-CPGCG-GCPGCN pHTT7f1-NHα(CCGPCCN), encodes α-CCGPCCN ("α-GP")

pHTT7f1-NHα(CCPGCCN), encodes α-CCPGCCN ("α-PG")

pHTT7f1-NHα(CCPGPCCN), encodes α-CCPGPCCN ("α-PGP")

pHTT7f1-NHα(CCGPGCCN), encodes α-CCGPGCCN ("α-GPG")

pHTT7f1-NHα(CCPGPGCCN), encodes α-CCPGPGCCN ("α-PGPG")

pHTT7f1-NHα(CCGPGPCCN), encodes α-CCGPGPCCN ("α-GPGP")

pHTT7f1-NHα-(SARP-P3/0-PP9), encodes α-CCPPPCC—PPPPPPPPP—CCCCN ("α-SARP—P3/0-PP9")

pHTT7f1-NHα-(SARP-P3/G1-PP9), encodes α-CCPP-PCC—PPPPPPPPP—CCGCCN ("α-SARP—P3/G1-PP9")

pHTT7f1-NHα-(SARP-P3/G1-PP12), encodes α-CCPP-PCC—PPPPPPPPPPPP—CCGCCN ("α-SARP-P3/G1-PP12")

pHTT7f1-NHα-(SARP-P4/G1-PP9), encodes α-CCPPP-PCC—PPPPPPPPP—CCGCCN ("α-SARP—P4/G1-PP9")

pHTT7f1-NHα-(SARP-P3/G1-HL4X), encodes α-CCPP-PCC-ANAAAKNAAAKNAAAKNAAAKA-CCGCCN ("α-SARP-P3/G1-HL4X")

pHTT7f1-NHα-(SARP-P3/G1-HL5X), encodes α-CCPP-PCC-ANAAAKNAAAKNAAAKNAAAKNAAAKA-CCGCCN ("α-SARP-P3/G1-HL5X")

15.2: Crude Lysates

Transformants of E. coli strain BL21(DE3) (Novagen) with pHTT7f1-NHα derivatives were shaken at 37° C. in 10 ml LB containing 2 mg/ml ampicillin until $OD_{600}=0.7$, induced by addition of IPTG to 1 mM, and further shaken for another 3 h at 37° C. Cells were harvested by centrifugation (4600×g; 5 min, 4° C.), and stored at −80° C. Immediately before use, cells were re-suspended in 600 µl 100 mM Tris-HCl, pH 7.9, 200 mM NaCl, 1 mM β-mercaptoethanol, 40 µl/ml 25×EDTA-free protease inhibitor cocktail (Roche Diagnostics, Inc.), and 20 µg/ml lysozyme, incubated 5 min at 4° C., and lysed by sonication. Lysates were cleared by centrifugation (16,000×g; 5 min at 4° C.). Concentration of α derivative: ~1 µM. Purity of α derivative: ~10%.

14.3: Purified Proteins

To cleared lysates (prepared as above, but from 50 ml cultures) was added 1 µl benzonase nuclease (Novagen), 2.8 µl 1 M imidazole and 0.2 ml Ni2+-NTA agarose (Qiagen). Following 15 min at 25° C., samples were transferred to 2 ml columns (Poly-Prep, BioRad, Inc.), washed with 10 ml buffer A (100 mM Tris-HCl, pH 7.9, 200 mM NaCl, 2 mM imidazole, and 5% glycerol), washed with 2 ml buffer A containing 10 mM imidazole, and eluted with 2×1 ml buffer A containing 40 mM imidazole. Samples were dialyzed against 100 mM Tris-HCl, pH 7.9, 200 mM NaCl, 1 mM β-mercaptoethanol, and 5% glycerol. Yield: ~300 µg. Purity: ~85%. Samples were stored at −80° C.

EXAMPLE 16

Probe-Tag Specificities: Peptides 16.1: Assay

Probe-tag specificities were defined using electrophoretic-mobility-shift assays. For each combination of probe and tetracysteine-tagged peptide, two reactions were performed in parallel: one reaction at 5 mM DTT, and one reaction at 50 mM DTT. Reaction mixtures contained (8 µl): 100 µM tetracysteine-tagged peptide (Example 14.1), 25 mM sodium phosphate (pH 7.4), 100 mM KCl, 1 mM tri(2-carboxyethyl)phosphine hydrochloride, 1 mM 2-mercaptoethanesulfonic acid, and 10% DMF. DTT (1 µl of 50 mM DTT for reactions at 5 mM DTT; 1 µl of 500 mM DTT for reactions at 50 mM DTT) was added, and samples were incubated 30 min at 25° C. FlAsH (Griffin, et al. (2000) Methods Enzmol. 327, 565-578), Cy3-(SO3)$_2$-(PAEDT)$_2$ (Example 8.2), Cy5-(SO3)$_2$-(PAEDT)$_2$ (Example 9.1), or Cy7-(SO$_3$)$_2$-(PAEDT)$_2$ (Example 9A.1) (1 µl of 0.1 mM in DMF) was added, and samples were incubated 30 min at 25° C. Non-denaturing loading buffer (BioRad, Inc.; 5 µl) was added, and 3 µl aliquots were analyzed by non-denaturing PAGE on 15% TBE gels (BioRad, Inc.), followed by x/y fluorescence scanning (for FlAsH, Molecular Dynamics FluorImager 595, with excitation=488 nm and emission=515-545 nm; for Cy3, Molecular Dynamics FluorImager 595, with excitation=514 nm and emission>570 nm; for Cy5 and Cy7, Molecular Dynamics Storm 860, with excitation=635 nm and emission>650 nm). Fluorescence intensities of probe-tag complexes were quantified and normalized to the fluorescence intensity of the probe-"GPG" complex in the reaction at 5 mM DTT.

16.2: Results: FlAsH

Figure 3:
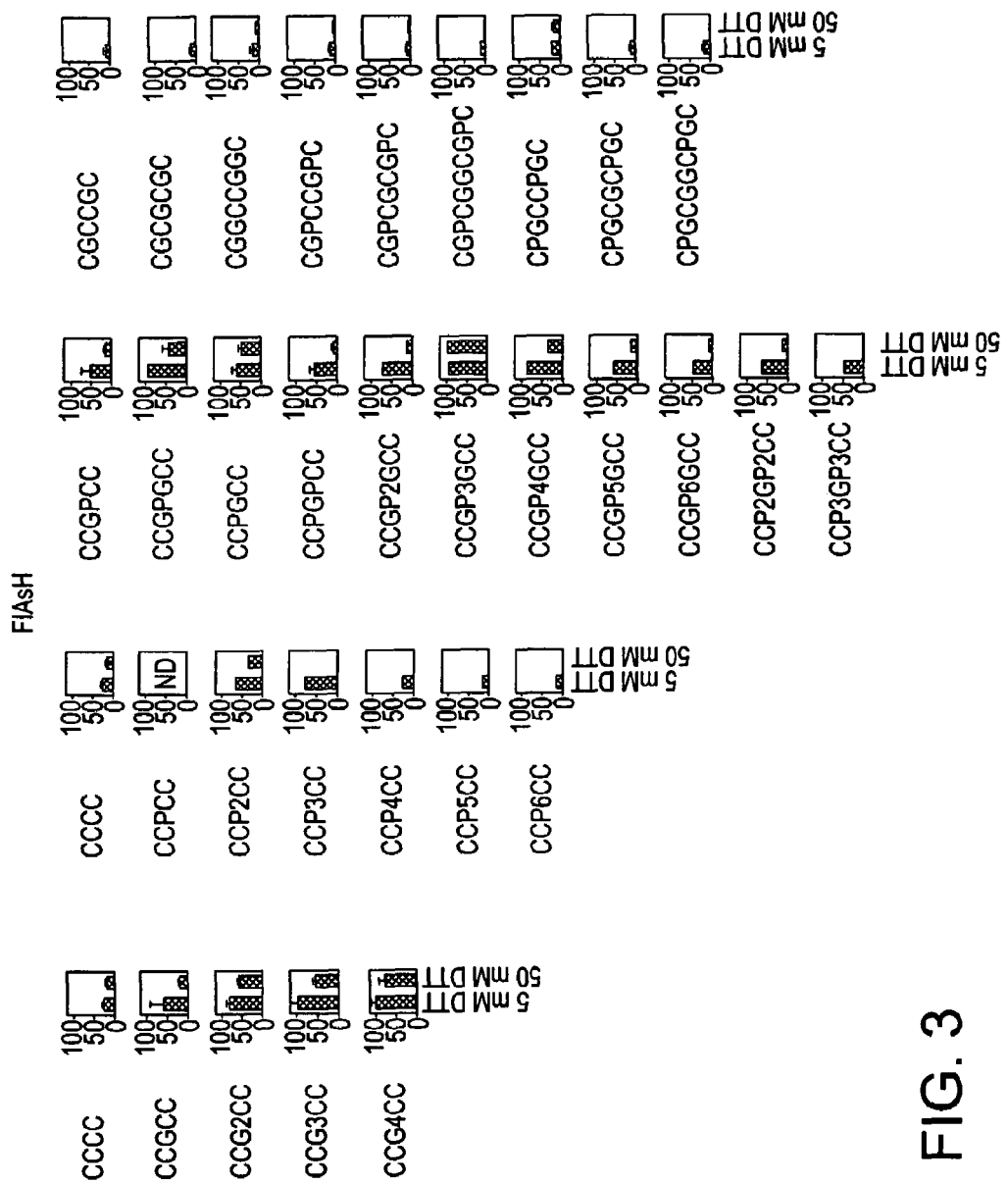
FIG. 3 depicts the results for FlAsH labeling of tetracysteine-tagged peptides.

Results for FlAsH labeling are presented in FIG. 3. Labeling of tetracysteine-tagged peptides was tag-dependent. In reactions in the presence of 5 mM DTT, strong labeling (normalized intensity≧60%) was obtained with "G1," "G2," "G3," "G4," "P2," "P3," "GPG," "GP2G," "GP3G," "GP4G," "GP5G," "PG," "PGP," and "P2GP2"; and moderately strong labeling (normalized intensity≧20%, <60%) was obtained with "0," "P4," "GP," "GP6G," and "P3GP3." In reactions in the presence of 50 mM DTT, strong labeling (normalized intensity≧50%) was obtained with "G2," "G3," "G4," "GP3G," and "PG"; and moderately strong labeling (normalized intensity≧10%, <50%) was obtained with "0," "G1," "P2," "GP," "GPG," "GP2G," "GP4G," "GPSG," and "CPGCCPGC."

16.3: Results: Cy3-(SO3)$_2$-(PAEDT)$_2$

Figure 4:
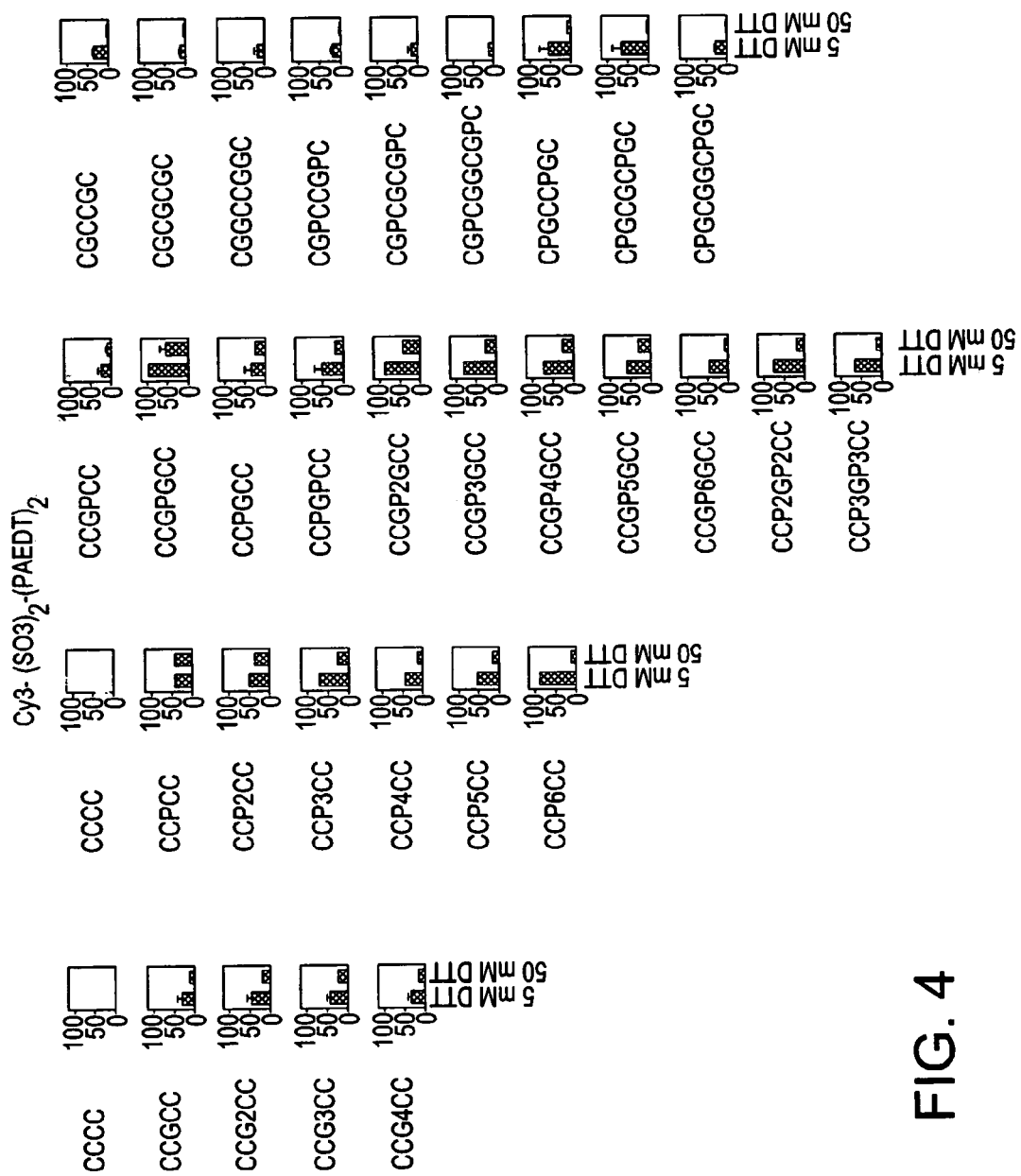
FIG. 4 depicts the results for Cy3-$(SO_3)_2$-(PAEDT) labeling of tetracysteine-tagged peptides.

Results for Cy3-(SO3)$_2$-(PAEDT) labeling are presented in FIG. 4. Labeling of tetracysteine-tagged peptides was tag-dependent. In reactions in the presence of 5 mM DTT, strong labeling (normalized intensity≧60%) was obtained with "P3", "P6", "GPG", "GP2G", "GP3G", "GP4G," "GPSG," "PGP" "P2GP2," and "P3GP3," and "CPGCGCPGC"; and moderately strong labeling (normalized intensity≧20%, <60%) was obtained with "G1," "G2," "G3," "G4," "P1", "P2," "P4," "P5", "GP", "GP6G", "PG", "PGP," "CGCCGC," "CGPCCGPC," "CPGCCPGC," and "CPGCGGCPGC." In reactions in the presence of 50 mM DTT, strong labeling (normalized intensity≧50%) was obtained with "GPG"; and moderately strong labeling (normalized intensity≧10%, <50%) was obtained with "G2," "G3," "G4," "P1," "P2," "P3," "P4," "P5," "GP2G," "GP3G," "GP4G," "GPSG," "PG," "PGP," "P2GP2," and "P3GP3."

16.4: Results: Cy5-(SO3)$_2$-(PAEDT)$_2$

Figure 5:
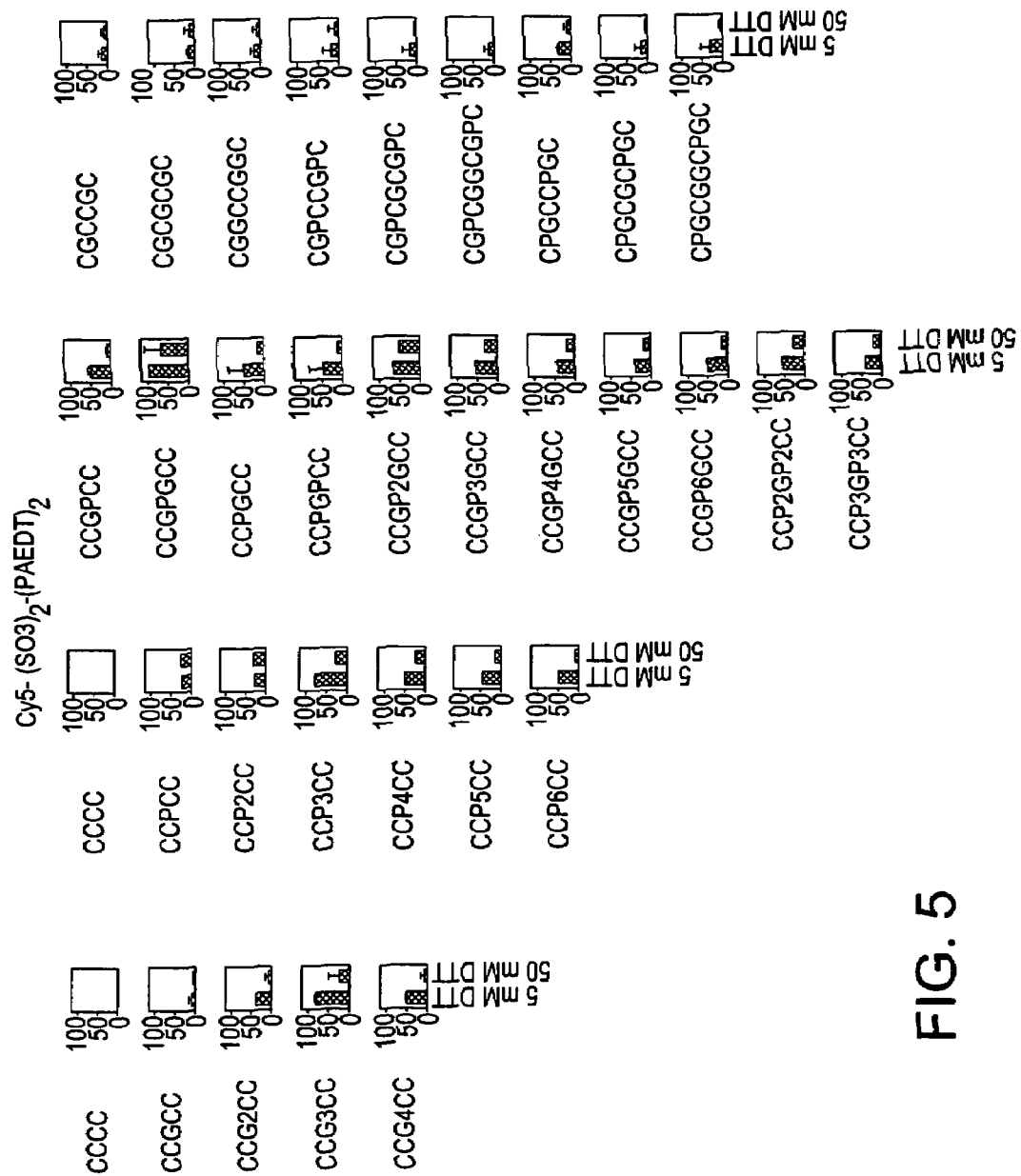
FIG. 5 depicts the results for Cy5-$(SO_3)_2$-(PAEDT) labeling of tetracysteine-tagged peptides.

Results for Cy5-(SO3)$_2$-(PAEDT) labeling are presented in FIG. 5. Labeling of tetracysteine-tagged peptides was tag-dependent. In reactions in the presence of 5 mM DTT, strong labeling (normalized intensity≧60%) was obtained with "G3," "P3," "GPG," and "GP2G"; and moderately strong labeling (normalized intensity≧20%, <60%) was obtained with "G2," "G4," "P2," "P4," "P5," "P6," "GP," "GP3G," "GP4G," "GP5G," "GP6G," "PG," "PGP," "P2GP2," "P3GP3," "CGPCCGPC," "CGPCGCGPC," "CPGCCPGC," and "CPGCGCPGC." In reactions in the presence of 50 mM DTT, strong labeling (normalized intensity≧50%) was obtained with "GPG" and "GP2G"; and moderately strong labeling (normalized intensity≧10%, <50%) was obtained with "G3," "G4," "P," "P2," "P3," "P4," "P5," "GP3G," "GP4G," "GP5G," "GP6G," "PG," "PGP," "P2GP2," "P3GP3,"[1] "CGCGCGC," and "CGPC-CGPC."

16.5: Results: Cy7-(SO3)$_2$-(PAEDT)$_2$

Figure 6:
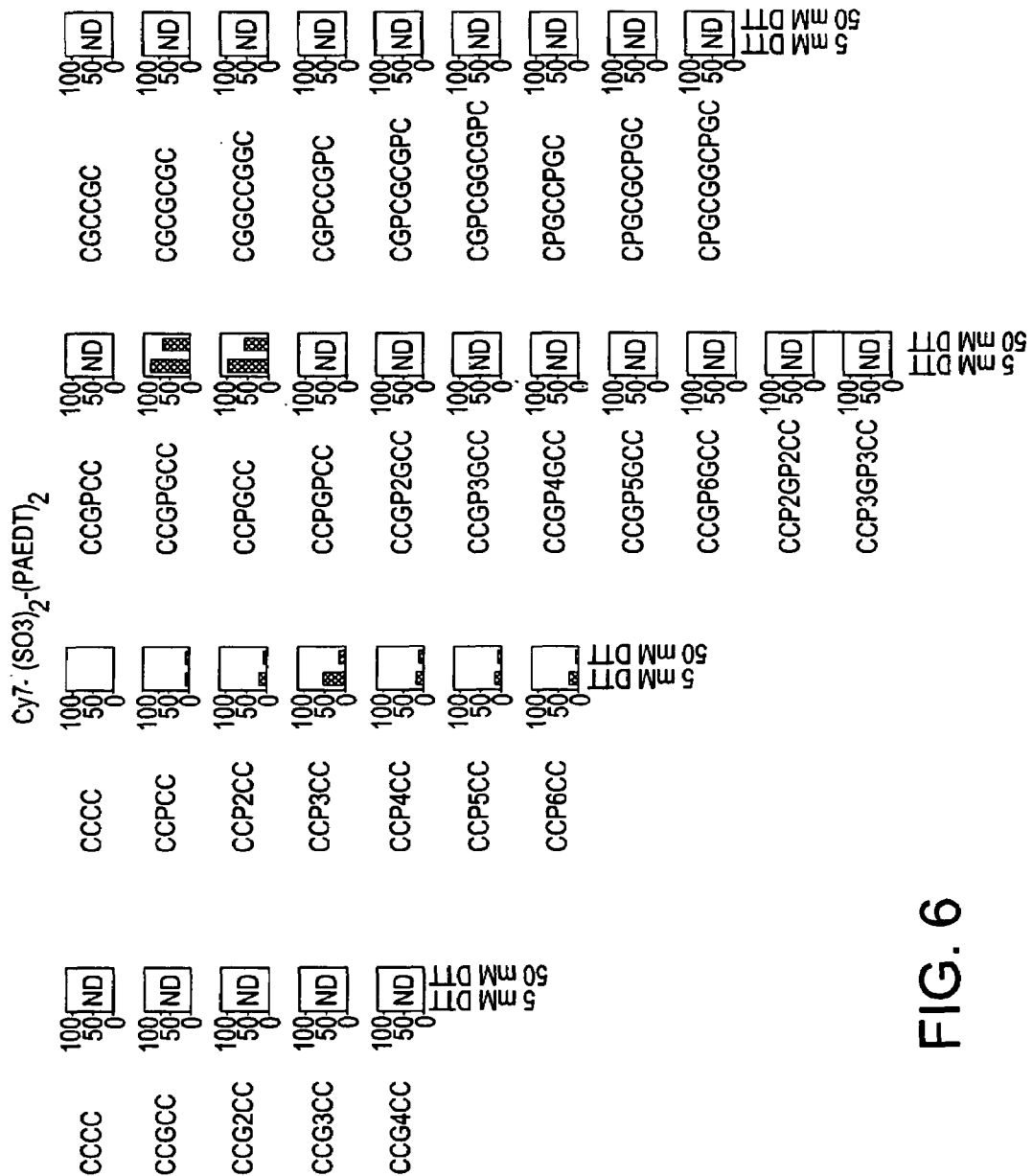
FIG. 6 depicts the results for Cy7-$(SO_3)_2$-(PAEDT) labeling of tetracysteine-tagged peptides.

Results for Cy7-(SO3)$_2$-(PAEDT) labeling are presented in FIG. 6. Labeling of tetracysteine-tagged peptides was tag-dependent. In reactions in the presence of 5 mM DTT, strong labeling (normalized intensity≧60%) was obtained with "GPG"; and moderately strong labeling (normalized intensity≧20%, <60%) was obtained with "P3," "P4," "P6," and "PG." In reactions in the presence of 50 mM DTT, strong labeling (normalized intensity≧50%) was obtained with "GPG"; and moderately strong labeling (normalized intensity≧10%. <50%) was obtained with "P3" and "PG."

EXAMPLE 17

Probe-Tag Specificities: Proteins 17.1: Assay

Probe-tag specificities were defined using electrophoretic-mobility-shift assays. For each combination of probe and tetracysteine-tagged protein, two reactions were performed in parallel: one reaction at 1 mM DTT, and one reaction at 10 mM DTT. DTT (1 µl of 100 mM DTT for reactions at 1 mM DTT, 1 µl of 1 M DTT for reactions at 10 mM DTT) was added to 97 µl crude lysate containing tetracysteine-tagged protein (~1 µM; Example 15.2), and samples were incubated 30 min at 25° C. FlAsH (Griffin, et al. (2000) Methods Enzmol. 327, 565-578), Cy3-(SO3)$_2$-(PAEDT)$_2$ (Example 8.2), or Cy5-(SO3)$_2$-(PAEDT)$_2$ (Example 9.1) (2 µl of 1 mM in DMF) was added, and samples were incubated 30 min at 25° C. 15 µl aliquots were mixed with 5 µl 0.25 M Tris-HCl, pH 6.8, 2% SDS, 0.01% bromophenol blue, and 30% glycerol and analyzed by SDS-PAGE on 4-20% gradient gels (BioRad, Inc.), followed by x/y fluorescence scanning (for FlAsH, Molecular Dynamics FluorImager 595, with excitation=488 nm and emission=515-545 nm; for Cy3, Molecular Dynamics FluorImager 595, with excitation=514 nm and emission≧570 nm; for Cy5 and Cy7, Molecular Dynamics Storm 860, with excitation=635 nm and emission≧650 nm). Fluorescence intensities of probe-tag complexes were quantified and normalized to the fluorescence intensity of the probe-"GPG" complex in the reaction at 1 mM DTT.

17.2: Results: FlAsH

Figures 7, 8, 9:
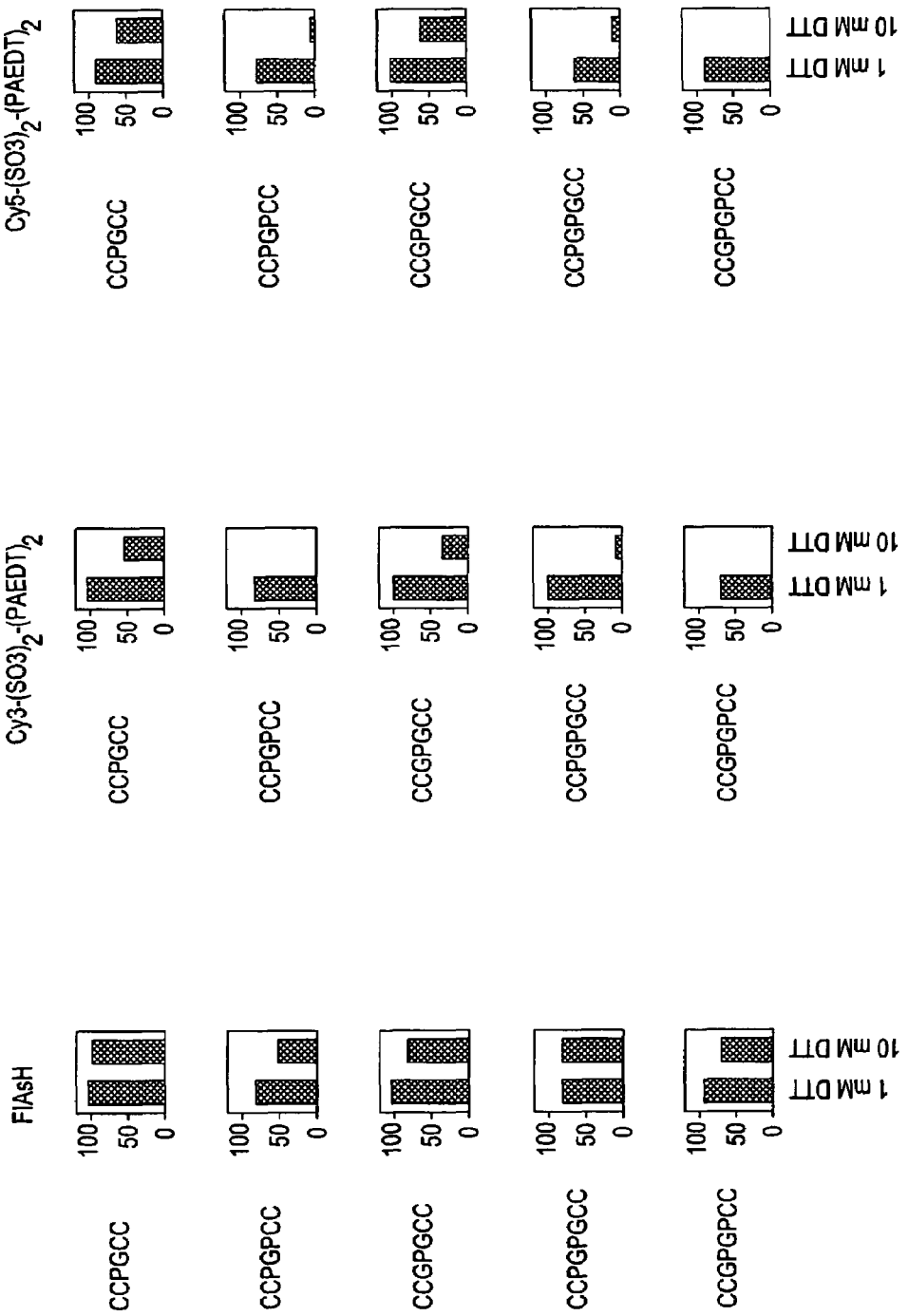
FIG. 7 depicts the results for FlAsH labeling of tetracysteine-tagged protein.
FIG. 8 depicts the results for Cy3-$(SO_3)_2$-$(PAEDT)_2$ labeling of tetracysteine-tagged protein.
FIG. 9 depicts the results for Cy5-$(SO_3)_2$-$(PAEDT)_2$ labeling of tetracysteine-tagged protein.

Results for FlAsH labeling are presented in FIG. 7. Labeling of tetracysteine-tagged protein was tag-dependent. In reactions in the presence of 1 mM DTT, strong labeling (normalized intensity≧60%) was obtained with "GPG," "GPGP," "PG," "PGP," and "PGPG." In reactions in the presence of 10 mM DTT, strong labeling (normalized intensity≧50%) was obtained with "GPG," "GPGP," "PG," and "PGPG"; and moderately strong labeling (normalized intensity≧10%, <50%) was obtained with "PGP."

17.3: Results: Cy3-(SO3)$_2$-(PAEDT)$_2$

Results for Cy3-(SO3)$_2$-(PAEDT)$_2$ labeling are presented in FIG. 8. Labeling of tetracysteine-tagged protein was tag-dependent. In reactions in the presence of 1 mM DTT, strong labeling (normalized intensity≧60%) was obtained with "GPG," "GPGP," "PG," "PGP," and "PGPG." In reactions in the presence of 10 mM DTT, strong labeling (normalized intensity≧50%) was obtained with "PG"; and moderately strong labeling (normalized intensity≧10%, <50%) was obtained with "GPG."

17.4: Results: Cy5-(SO3)$_2$-(PAEDT)$_2$

Results for Cy5-(SO3)$_2$-(PAEDT)$_2$ labeling are presented in FIG. 9. Labeling of tetracysteine-tagged protein was tag-dependent. In reactions in the presence of 1 mM DTT, strong labeling (normalized intensity≧60%) was obtained with "GPG," "GPGP," "PG," and "PGP"; and moderately strong labeling (normalized intensity≧10%, <50%) was obtained with "PGPG." In reactions in the presence of 10 mM DTT, strong labeling (normalized intensity≧50%) was obtained with "GPG" and "PG."

EXAMPLE 18

Multicolor, Multisite Labeling: Pairs of Peptides 18.1: Assay

Multicolor, multisite labeling was assessed in electrophoretic-mobility-shift assays. Pairs of tetracysteine-tagged peptides—one neutral tetracysteine-tagged peptide, and one negatively-charged tetracysteine-tagged peptide (the charge difference resulting in different electrophoretic mobilities on the gel, thus allowing the two tetracysteine-tagged peptides to be distinguished)—were analyzed. For each combination of probe and pair of tetracysteine-tagged peptides, three reactions were performed in parallel: one reaction at 5 mM DTT, one reaction at 10 mM DTT, and one reaction at 20 mM DTT. Reaction mixtures contained (7 µl): 50 µM neutral tetracysteine-tagged peptide (Example 14.1, set A), 50 µM negatively-charged tetracysteine-tagged peptide (Example 14.1, set B), 25 mM sodium phosphate (pH 7.4), 100 mM KCl, 1 mM tri(2-carboxyethyl)phosphine hydrochloride, 1 mM 2-mercaptoethanesulfonic acid, and 10% DMF. DTT (1 µl of 50 mM DTT for reactions at 5 mM DTT, 1 µl of 100 mM DTT for reactions at 10 mM DTT, and 1 µl of 200 mM DTT for reactions at 20 mM DTT) was added, and samples were incubated 30 min at 25° C. Cy5-(SO3)$_2$-(PAEDT)$_2$ (Example 9.1; 2 µl of 0.1 mM solution in DMF) was added, and samples were incubated 10 min at 25° C. FlAsH (Griffin, et al. (2000) Methods Enzmol. 327, 565-578; 2 µl of 0.1 mM solution in DMF) was then added, and samples were further incubated 20 min at 25° C. Non-denaturing loading buffer (BioRad, Inc.; 5 µl) was added, and 5 µl aliquots were analyzed by non-denaturing PAGE on 15% TBE gels (Bio-Rad, Inc.) followed by x/y fluorescence scanning (for FlAsH detection, Molecular Dynamics FluorImager 595, with excitation=488 nm and emission=515-545 nm; for Cy5 detection, Molecular Dynamics Storm 860, with excitation=635 nm and emission≧650 nm).

18.2: Results: FlAsH and Cy5-(SO3)$_2$-(PAEDT)$_2$ with "G1$^O$" and "P3"

Figure 10:
FIG. 10 depicts the results for multicolor, multisite labeling with probes FlAsH and Cy5-$(SO_3)_2$-$(PAEDT)_2$ and tetracysteine-tagged peptides G1° and P3.

Results for multicolor, multisite labeling with probes FlAsH and Cy5-(SO3)$_2$-(PAEDT)$_2$ and tetracysteine-tagged peptides "G1$^O$" and "P3" are presented in FIG. 10. FlAsH and Cy5-(SO3)$_2$-(PAEDT)$_2$ exhibited orthogonal specificities. FlAsH labeled "G1$^O$" and did not significantly label "P3" (<<10% level of labeling of "G1$^O$"). Cy5-(SO3)$_2$-(PAEDT)$_2$ labeled "P3" and did not significantly label "G1$^O$" (<<10% level of labeling of "P3").

18.3: Results: FlAsH and Cy5-(SO3)$_2$-(PAEDT)$_2$ with "G1$^O$" and "P4"

Results for multicolor, multisite labeling with probes FlAsH and Cy5-(SO3)$_2$-(PAEDT)$_2$ and tetracysteine-tagged peptides "G1$^O$" and "P4" were comparable to results for multicolor, multisite labeling with probes FlAsH and Cy5-(SO3)$_2$-(PAEDT)$_2$ and tetracysteine-tagged peptides "G1" and "P3" (Example 18.2; FIG. 10). FlAsH and Cy5-(SO3)$_2$-(PAEDT)$_2$ exhibited orthogonal specificities. FlAsH labeled "G1$^O$" and did not significantly label "P4" (<<10% level of labeling of "G1$^O$"). Cy5-(SO3)$_2$-(PAEDT)$_2$ labeled "P4" and did not significantly label "G1$^O$" (<<10% level of labeling of "P4").

18.4: Results: FlAsH and Cy5-(SO3)$_2$-(PAEDT)$_2$ with "G1$^O$" and "P5"

Results for multicolor, multisite labeling with probes FlAsH and Cy5-(SO$_3$)$_2$-(PAEDT)$_2$ and tetracysteine-tagged peptides "G1$^O$" and "P5" were comparable to results for multicolor, multisite labeling with probes FlAsH and Cy5-(SO3)$_2$-(PAEDT)$_2$ and tetracysteine-tagged peptides "G1$^O$" and "P3" (Example 18.2; FIG. 10). FlAsH and Cy5-(SO3)$_2$-(PAEDT)$_2$ exhibited orthogonal specificities. FlAsH labeled "G1$^O$" and did not significantly label "P5" (<<10% level of labeling of "G1$^O$"). Cy5-(SO3)$_2$-(PAEDT)$_2$ labeled "P5" and did not significantly label "G1$^O$" (<<10% level of labeling of "P5").

18.5: Results: FLAsH and Cy5-(SO3)$_2$-(PAEDT)$_2$ with "G1$^O$" and "P6"

Results for multicolor, multisite labeling with probes FlAsH and Cy5-(SO3)$_2$-(PAEDT)$_2$ and tetracysteine-tagged peptides "G1$^O$" and "P6" were comparable to results for multicolor, multisite labeling with probes FlAsH and Cy5-(SO3)$_2$-(PAEDT)$_2$ and tetracysteine-tagged peptides "G1" and "P3" (Example 18.2; FIG. 10). FlAsH and Cy5-(SO3)$_2$-(PAEDT)$_2$ exhibited orthogonal specificities. FlAsH labeled "G1" and did not significantly label "P6" (<<10% level of labeling of "G1$^O$"). Cy5-(SO3)$_2$-(PAEDT)$_2$ labeled "P6" and did not significantly label "G1$^O$" (<<10% level of labeling of "P6").

EXAMPLE 19

Multicolor, Multisite Labeling: Single Peptides (Self-Assembled Relay Probes, SARPs)

19.1: Assay

Multicolor, multisite labeling of doubly-tetracysteine-tagged peptides—yielding self-assembled relay probes, SARPs—was assessed in electrophoretic-mobility-shift assays. Reaction mixtures contained (16 µl): 100 µM doubly-tetracysteine-tagged peptide (Example 14.1, set C), 25 mM sodium phosphate (pH 7.4), 100 mM KCl, 1 mM tri(2-carboxyethyl)phosphine hydrochloride, 1 mM 2-mercaptoethanesulfonic acid, and 10% DMF. DTT (2 µl of 50 mM solution) was added, and samples were incubated 30 min at 25° C. Cy5-(SO3)$_2$-(PAEDT)$_2$ (Example 9.1; 1 µl of 1 mM solution in DMF) was added, and samples were incubated 10 min at 25° C. FlAsH (Griffin, et al. (2000) Methods Enzmol. 327, 565-578; 1 µl of 1 mM solution in DMF) was then added, and samples were further incubated 20 min at 25° C. 5 µl aliquots were mixed with 5 µl non-denaturing loading buffer (BioRad, Inc.) and analyzed by PAGE on 4-20% TBE gels (BioRad, Inc.) followed by x/y fluorescence scanning [for FlAsH detection, Molecular Dynamics FluorImager 595, with excitation at 488 nm and emission 515-545 nm; for Cy5 detection, Molecular Dynamics Storm 860, with excitation=635 nm and emission≧650 nm; for FlAsH-Cy5-FRET-dependent detection (SARP detection), Molecular Dynamics FluorImager 595 and Chroma D680/30M filter, with excitation=488 nm and emission≧680 nm)].

19.2: Results: FlAsH and Cy5-(SO3)$_2$-(PAEDT)$_2$ with "SARP-P4/G1-PP9"

Figure 11:
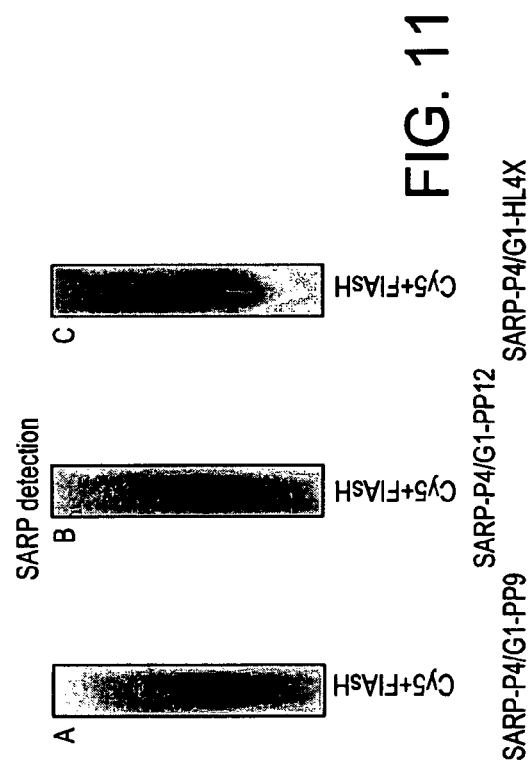
FIG. 11 depicts the results for multicolor, multisite labeling with probes FlAsH and Cy5-$(SO_3)_2$-$(PAEDT)_2$ and doubly-tetracysteine-tagged peptides "SARP-P4/G1-PP9" (A), "SARP-P4/G1-PP12" (B) or "SARP-P4/G1-HL4X" (C).

Results for multicolor, multisite labeling with probes FlAsH and Cy5-(SO3)$_2$-(PAEDT)$_2$ and doubly-tetracysteine-tagged peptides "SARP-P4/G1-PP9" are presented in FIG. 11A. FlAsH and Cy5-(SO3)$_2$-(PAEDT)$_2$ co-labeled "SARP-P4/G1-PP9" and participated in FlAsH-Cy5 FRET within the resulting complex, as documented by x/y fluorescence scanning with FlAsH-Cy5-FRET-dependent detection (SARP detection). Control experiments omitting FlAsH or omitting Cy5-(SO3)$_2$-(PAEDT)$_2$ yielded no signal or a significantly lower signal, respectively.

19.3: Results: FlAsH and Cy5-(SO3)$_2$-(PAEDT)$_2$ with "SARP-P4/G1-PP12"

Results for multicolor, multisite labeling with probes FlAsH and Cy5-(SO3)$_2$-(PAEDT)$_2$ and doubly-tetracysteine-tagged peptides "SARP-P4/G1-PP12" are presented in FIG. 11B. FlAsH and Cy5-(SO3)$_2$-(PAEDT)$_2$ co-labeled "SARP-P4/G1-PP12" and participated in FlAsH-Cy5 FRET within the resulting complex, as documented by x/y fluorescence scanning with FlAsH-Cy5-FRET-dependent detection (SARP detection). Control experiments omitting FlAsH or omitting Cy5-(SO3)$_2$-(PAEDT)$_2$ yielded no signal or a significantly lower signal, respectively.

19.4: Results: FlAsH and Cy5-(SO3)$_2$-(PAEDT)$_2$ with "SARP-P4/G1-HL4X"

Results for multicolor, multisite labeling with probes FlAsH and Cy5-(SO$_3$)$_2$-(PAEDT)$_2$ and doubly-tetracysteine-tagged peptides "SARP-P4/G1-HL4X" are presented in FIG. 11C. FlAsH and Cy5-(SO3)$_2$-(PAEDT)$_2$ co-labeled "SARP-P4/G1-HL4X" and participated in FlAsH-Cy5 FRET within the resulting complex, as documented by x/y fluorescence scanning with FlAsH-Cy5-FRET-dependent detection (SARP detection). Control experiments omitting FlAsH or omitting Cy5-(SO3)$_2$-(PAEDT)$_2$ yielded no signal or a significantly lower signal, respectively.

EXAMPLE 20

Multicolor, Multisite Labeling: Single Proteins (Self-Assembled Relay Probes, SARPs)

20.1: Assay

Multicolor, multisite labeling of doubly-tetracysteine-tagged proteins—yielding self-assembled relay probes, SARPs—was assessed in electrophoretic-mobility-shift assays. DTT (1 µl of 125 mM solution) was added to 23 µl crude lysate containing doubly-tetracysteine-tagged protein (~1 µM; Example 14.2), and samples were incubated 30 min at 25° C. Cy5-(SO3)$_2$-(PAEDT)$_2$ (Example 9.2; 0.5 µl of 1 mM solution in DMF) was added, and samples were incubated 20 min at 25° C. FlAsH (Griffin, et al. (2000) Methods Enzmol. 327, 565-578; 0.5 µl of 0.1 mM solution in DMF)

was then added, and samples were further incubated 5 min at 25° C. 5 μl aliquots were mixed with 5 μl 0.25 M Tris-HCl, pH 6.8, 2% SDS, 0.01% bromophenol blue, and 30% glycerol, and analyzed by SDS-PAGE on 4-20% gradient gels (BioRad, Inc.) followed by x/y fluorescence scanning [for FlAsH detection, Molecular Dynamics FluorImager 595, with excitation=488 nm and emission≧645 nm; for Cy5 detection, Molecular Dynamics Storm 860, with excitation=635 nm and emission≧650 nm; for FlAsH-Cy5-FRET-dependent detection (SARP detection), Molecular Dynamics FluorImager 595 and Chroma D680/30M filter, with excitation=488 nm and emission≧680 nm].

20.2: Results: FlAsH and Cy5-(SO3)$_2$-(PAEDT)$_2$ with "α-SARP-P3/G1-PP9"

Figure 12:
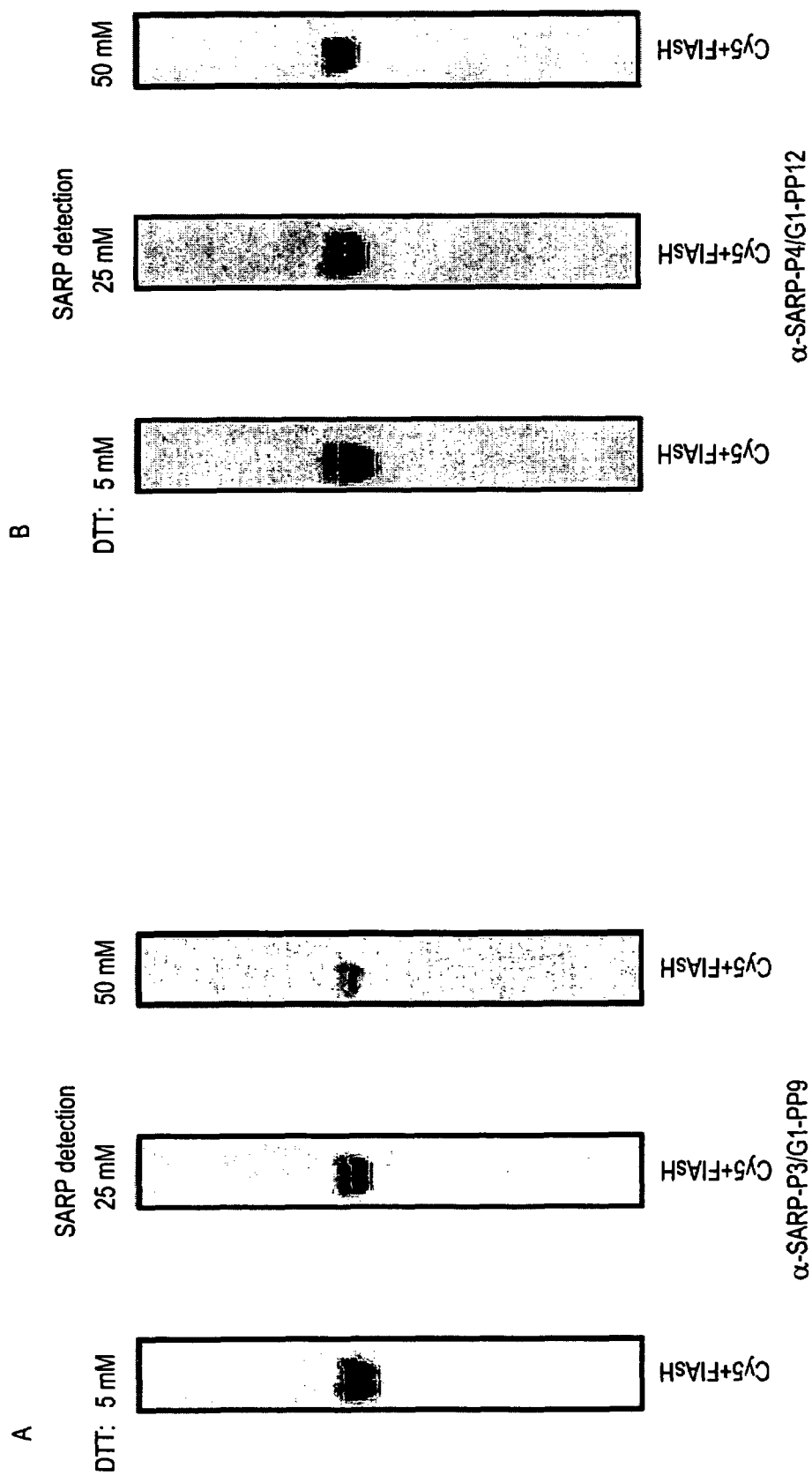
FIG. 12 depicts the results for multicolor, multisite labeling with probes FlAsH and Cy5-$(SO_3)_2$-$(PAEDT)_2$ and doubly-tetracysteine-tagged protein "α-SARP-P3/G1-PP9" (A) or "α-SARP-P4/G1-PP9" (B).

Results for multicolor, multisite labeling with probes FlAsH and Cy5-(SO$_3$)$_2$-(PAEDT)$_2$ and doubly-tetracysteine-tagged protein "α-SARP-P3/G1-PP9" are presented in FIG. 12A. FlAsH and Cy5-(SO3)$_2$-(PAEDT)$_2$ co-labeled "α-SARP-P3/G1-PP9" and participated in FlAsH-Cy5 FRET within the resulting complex, as documented by x/y fluorescence scanning with FlAsH-Cy5-FRET-dependent detection (SARP detection). Control experiments omitting FlAsH or omitting Cy5-(SO3)$_2$-(PAEDT)$_2$ yielded no signal or a significantly lower signal, respectively. FlAsH and Cy5-(SO3)$_2$-(PAEDT)$_2$ co-labeling and FlAsH-Cy5-FRET-dependent detection was highly specific. Thus, no other protein in the crude lysate was detectably labeled.

20.3: Results: FlAsH and Cy5-(SO3)$_2$-(PAEDT)$_2$ with "α-SARP-P4/G1-PP9"

Results for multicolor, multisite labeling with probes FlAsH and Cy5-(SO3)$_2$-(PAEDT)$_2$ and doubly-tetracysteine-tagged protein "α-SARP-P4/G1-PP9" are presented in FIG. 12B. FlAsH and Cy5-(SO3)$_2$-(PAEDT)$_2$ co-labeled "α-SARP-P4/G1-PP9" and participated in FlAsH-Cy5 FRET within the resulting complex, as documented by x/y fluorescence scanning with FlAsH-Cy5-FRET-dependent detection (SARP detection). Control experiments omitting FlAsH or omitting Cy5-(SO3)$_2$-(PAEDT)$_2$ yielded no signal or a significantly lower signal, respectively. FlAsH and Cy5-(SO3)$_2$-(PAEDT)$_2$ co-labeling and FlAsH-Cy5-FRET-dependent detection was highly specific. Thus, no other protein in the crude lysate was detectably labeled.

What is claimed is:

1. A detectable complex comprising:
   (a) at least one target material;
   (b) a first peptide tag bound to said at least one target material;
   (c) a second peptide tag bound to said at least one target material, wherein the second peptide tag is different from said first peptide tag;
   (d) a first conjugate having a detectable group and two pendant phenylarsine moieties comprising a first tag binding group; wherein said first conjugate preferentially associates with said first peptide tag;
   (e) a second conjugate having a detectable group and two pendant phenylarsine moieties comprising a second tag binding group; wherein said second conjugate preferentially associates with said second peptide tag;
   wherein the mean distance and/or mean angle between said pendant phenylarsine moieties in said first conjugate is different from the mean distance and/or mean angle between said pendant phenylarsine moieties in said second conjugate; and
   wherein at least one of said first and second conjugates is represented by the general structural Formula (I):

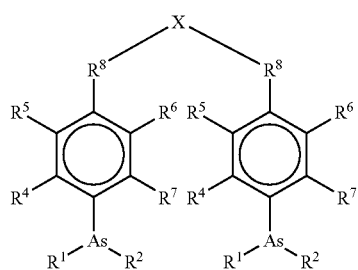

wherein:
(i) $R^1$ and $R^2$, together with the arsenic atom, form a ring according to the general structural Formula (IIB),:

wherein

Z represents a hydrocarbon chain comprising 2-4 singly or doubly bonded carbon atoms wherein each carbon atom may be further substituted with one or more groups selected from hydrogen, methyl, ethyl, 1-propyl, 2-propyl, methoxy, hydroxy, amino, carboxy, sulfo, oxo, thiol, halo (fluoro, chloro, bromo, or fluoro), $(CH_2)_{n''}SO_3-$ and $(CH_2)_{n''}SO_3H$, wherein n" is 1 or (ii) $R^4$, $R^5$, $R^6$ and $R^7$ are each independently H, F, $OR^3$, $R^3$, OAc, $NH_2$, $N(C_1-C_4\ alkyl)_2$; or $R^4$ with $R^5$, or $R^6$ together with $R^7$, or both, form a ring;

(iii) R⁸ is a linear or branched optionally substituted spacer having a minimum length of approximately 1.5 Ångstroms and a maximum length of approximately 15 Ångstroms; and (iv) X is cyanine.

2. The complex of claim 1, wherein said first peptide tag is bound to a first target material and said second peptide tag is bound to a second target material.

3. The complex of claim 1, wherein R¹ and R², together with the arsenic atom, form a ring according to the general Formula (IIB) when Z is CH₂SO₃— or CH₂SO₃H.

4. The complex of claim 1, wherein X is a cyanine fluorescent moiety selected from the group consisting of:

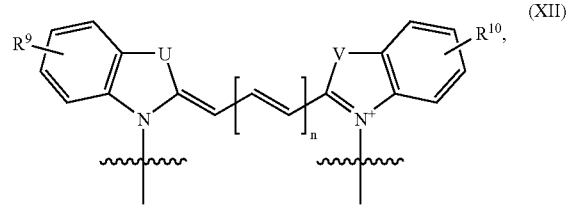
(XII)

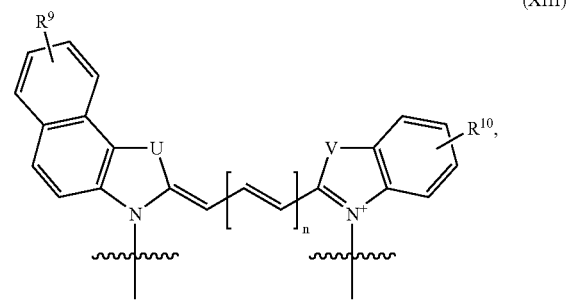
(XIII)

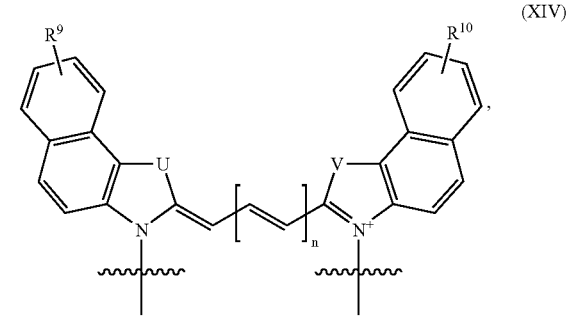
(XIV)

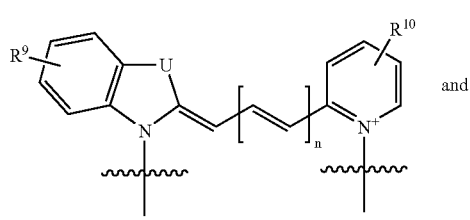
(XV)
and

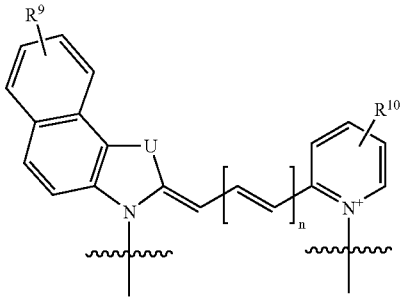
(XVI)

wherein U and V are each independently C(R¹⁴)₂, NH, O or S; R⁹ and R¹⁰ are each independently H or sulfonate; R¹⁴ is H, CH₃, CH₂CH₃, or (CH₂)₂CH₃; and n is 0 or an integer of from 1 to 6.

5. The complex of claim 4, wherein the value selected for n in Formulae XII-XVI can be varied such that at least the mean distance between said pendant phenylarsine moieties in said first and/or said second conjugates changes.

6. The complex of claim 1, wherein at least one of said first and second peptide tags with which a conjugate of Formula (I) preferentially associates is of the form C(X)ᵢC(X)ⱼC(X)ₖC, wherein C is cysteine, X is any amino acid, and i, j, and k are each independently selected from 0 or an integer from 1-8; provided that i, j, and k are not all zero.

7. The complex of claim 6, wherein at least one of said first and second peptide tags has a sequence of the form: CC(P)ₙCC, wherein C is Cysteine; P is Proline; and n is an integer from 3 to 8.

8. The complex of claim 6, wherein at least one of said first and second peptide tags is selected from the group consisting of CCPPPCC (SEQ ID NO: 1); CCPPPPCC (SEQ ID NO: 2); CCPPPPPCC (SEQ ID NO: 3); CCPPPPPPCC (SEQ ID NO: 4); and CCPGPCC (SEQ ID NO: 5).

9. The complex of claim 6, wherein the values of i, j and k for said first peptide tag are such that said first peptide tag interacts tightly with said first conjugate, but does not interact, or interacts less tightly with said second conjugate.

10. The complex of claim 6, wherein the values of i, j and k for said second peptide tag are such that said second peptide tag interacts tightly with said second conjugate, but does not interact, or interacts less tightly with said first conjugate.

11. The complex of claim 1, wherein said first conjugate is represented by the general structural Formula (I), and wherein said second conjugate is represented by the general structural Formula (II);

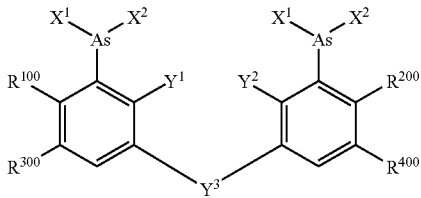
(II)

wherein each X¹ or X², independently is Cl, Br, I, ORᵃ, or SRᵃ, or X¹ and X² together with the arsenic atom form a ring having the structure:

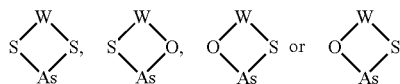

$R^a$ is H, $C_1$-$C_4$ alkyl, $CH_2CH_2OH$, $CH_2COOH$, or CN;

W is 1,2-ethanediyl, 1,2-propanediyl, 2,3-butanediyl, 1,3-propanediyl, 1,2-benzenediyl, 4-methyl-1,2-benzenediyl, 1,2-cyclopentanediyl, 1,2-cyclohexanediyl, 3-hydroxy-1,2-propanediyl, 3-sulfo-1,2-propanediyl, or 1,2-bis (carboxy)-1,2-ethanediyl;

$Y^1$ and $Y^2$, independently, are H or $CH_3$; or $Y^1$ and $Y^2$, together form a ring such that the biarsenical molecule has the general structure formula:

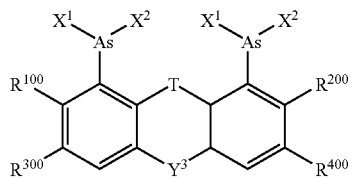

wherein T is O, S, $CH_2$, $C(CH_3)_2$, or NH;

$R^{100}$ and $R^{200}$, independently, are $OR^a$, OAc, $NR^aR^b$, or H;

$R^{300}$ and $R^{400}$, independently, are H, F, Cl, Br, I, $OR^a$, or $R^a$; or $R^{100}$ together with $R^{300}$, or $R^{200}$ together with $R^{400}$, or both, form a ring in which
  (i) one of $R^{100}$ or $R^{300}$ is $C_2$-$C_3$ alkyl and the other is $NR^a$ and
  (ii) one of $R^{200}$ and $R^{400}$ is $C_2$-$C_3$ alkyl and the other is $NR^a$;

$R^b$ is H, $C_1$-$C_4$ alkyl, $CH_2CH_2OH$, $CH_2COOH$, or CN;

$Y^3$ is $CR^aR^b$), $Cr^aOR^b$, C=O, or a spirolactone having one of the structures:

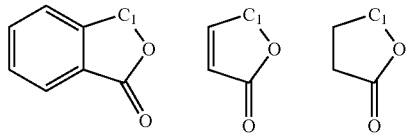

wherein the spiro linkage is formed at $C_1$.

12. The complex of claim 11, wherein said second conjugate is substituted at one or more positions of Formula II so as to add a signal generating detectable group selected from fluorescein, resorufin and derivatives thereof.

13. The complex of claim 11, wherein said first peptide tag interacts with said first conjugate represented by Formula (I), but does not interact substantially with said second conjugate represented by Formula (II).

14. The complex of claim 13, wherein said first peptide tag is of the form $C(X)_iC(X)_jC(X)_kC$, wherein C is cysteine, X is any amino acid, and i, j, and k are each independently selected from 0 or an integer from 1-8; provided that i, j and k are not all zero.

15. The complex of claim 14, wherein said first peptide tag has a sequence of the form: $CC(P)_nCC$, wherein C is cysteine; P is proline; and n is an integer from 3 to 8.

16. The complex of claim 14, wherein said first peptide tag is selected from the group consisting of CCPPPCC (SEQ ID NO: 1); CCPPPPCC(SEQ ID NO: 2); CCPPPPPCC (SEQ ID NO: 3); CCPPPPPPCC(SEQ ID NO: 4); and CCPGPCC (SEQ ID NO: 5).

17. The complex of claim 14, wherein said first peptide tag has a sequence of the form: $CC(P)_nCC$, wherein C is cysteine, P is proline; and n is an integer from 3 to 8; and said first conjugate is selected from the group consisting of Cy3 bis-sulfonato bis-propionamido-phenylarsine-ethanedithiol, Cy3 bis-propionamido-phenylarsine-ethanedithiol, Cy5 bis-sulfonato bis-propionamido-phenylarsine-ethanedithiol, Cy5 bis-propionamido-phenylarsine-ethanedithiol and Cy5 bis-sulfonato bis-propionamido-phenylarsine-ethanedithiol.

18. The complex of claim 14, wherein said second peptide tag interacts with said second fluorochrome conjugate represented by Formula (II) and is of the form $C(X)_iC$, wherein X is any amino acid, C is cysteine, and i is 2-6, provided that said second peptide tag includes at least four cysteine residues.

19. The complex of claim 18, wherein said second peptide tag is selected from the group consisting of CCCC (SEQ ID NO: 11) and CCGCC (SEQ ID NO: 12).

20. The complex of claim 1, wherein the mean distance and/or mean angle between said pendant phenylarsine moieties in said first conjugate is at least about 1.5 Angstroms greater than the mean distance and/or mean angle between said pendant phenylarsine moieties in said second conjugate.

21. The complex of claim 1, further comprising a third peptide tag bound to said at least one target material; and a third conjugate having a detectable group and two pendant phenylarsine moieties comprising a third tag binding group, wherein the mean distance and/or mean angle between said pendant moieties in said third conjugate is different from that in said first conjugate, and wherein said third peptide tag is different from said first and second peptide tags.

* * * * *

UNITED STATES PATENT AND TRADEMARK OFFICE
CERTIFICATE OF CORRECTION

PATENT NO. : 7,381,572 B2 Page 1 of 1
APPLICATION NO. : 11/256900
DATED : June 3, 2008
INVENTOR(S) : Ebright et al.

It is certified that error appears in the above-identified patent and that said Letters Patent is hereby corrected as shown below:

In Column 37, Line 13,     now reads "wqs" should read --was--.

In Column 39, Line 1,     now reads "10.25M" should read --0.25M--.

In Column 39, Line 38,     now reads "a" should read --α--.

Signed and Sealed this

Twenty-first Day of October, 2008

JON W. DUDAS
*Director of the United States Patent and Trademark Office*

```
                        SEQUENCE LISTING

<160> NUMBER OF SEQ ID NOS: 12

<210> SEQ ID NO 1
<211> LENGTH: 7
<212> TYPE: PRT
<213> ORGANISM: Artificial Sequence
<220> FEATURE:
<223> OTHER INFORMATION: target sequence

<400> SEQUENCE: 1

Cys Cys Pro Pro Pro Cys Cys
1               5

<210> SEQ ID NO 2
<211> LENGTH: 8
<212> TYPE: PRT
<213> ORGANISM: Artificial sequence
<220> FEATURE:
<223> OTHER INFORMATION: target sequence

<400> SEQUENCE: 2

Cys Cys Pro Pro Pro Pro Cys Cys
1               5

<210> SEQ ID NO 3
<211> LENGTH: 9
<212> TYPE: PRT
<213> ORGANISM: Artificial sequence
<220> FEATURE:
<223> OTHER INFORMATION: target sequence

<400> SEQUENCE: 3

Cys Cys Pro Pro Pro Pro Pro Cys Cys
1               5

<210> SEQ ID NO 4
<211> LENGTH: 10
<212> TYPE: PRT
<213> ORGANISM: Artificial sequence
<220> FEATURE:
<223> OTHER INFORMATION: target sequence
```

```
<400> SEQUENCE: 4

Cys Cys Pro Pro Pro Pro Pro Pro Cys Cys
1               5                   10

<210> SEQ ID NO 5
<211> LENGTH: 7
<212> TYPE: PRT
<213> ORGANISM: Artificial sequence
<220> FEATURE:
<223> OTHER INFORMATION: target sequence

<400> SEQUENCE: 5

Cys Cys Pro Gly Pro Cys Cys
1               5

<210> SEQ ID NO 6
<211> LENGTH: 6
<212> TYPE: PRT
<213> ORGANISM: Artificial sequence
<220> FEATURE:
<223> OTHER INFORMATION: target sequence

<400> SEQUENCE: 6

Cys Cys Gly Pro Cys Cys
1               5

<210> SEQ ID NO 7
<211> LENGTH: 7
<212> TYPE: PRT
<213> ORGANISM: Artificial sequence
<220> FEATURE:
<223> OTHER INFORMATION: target sequence

<400> SEQUENCE: 7

Cys Gly Cys Gly Cys Gly Cys
1               5

<210> SEQ ID NO 8
<211> LENGTH: 8
<212> TYPE: PRT
<213> ORGANISM: Artificial sequence
<220> FEATURE:
<223> OTHER INFORMATION: target sequence

<400> SEQUENCE: 8

Cys Gly Pro Cys Cys Gly Pro Cys
1               5

<210> SEQ ID NO 9
<211> LENGTH: 9
<212> TYPE: PRT
<213> ORGANISM: Artificial sequence
<220> FEATURE:
<223> OTHER INFORMATION: target sequence

<400> SEQUENCE: 9

Cys Gly Pro Cys Gly Cys Gly Pro Cys
1               5

<210> SEQ ID NO 10
<211> LENGTH: 10
<212> TYPE: PRT
<213> ORGANISM: Artificial sequence
<220> FEATURE:
<223> OTHER INFORMATION: target sequence

<400> SEQUENCE: 10
```

```
Cys Gly Pro Cys Gly Gly Cys Gly Pro Cys
1               5                   10

<210> SEQ ID NO 11
<211> LENGTH: 4
<212> TYPE: PRT
<213> ORGANISM: Artificial sequence
<220> FEATURE:
<223> OTHER INFORMATION: target sequence

<400> SEQUENCE: 11

Cys Cys Cys Cys
1

<210> SEQ ID NO 12
<211> LENGTH: 5
<212> TYPE: PRT
<213> ORGANISM: Artificial sequence
<220> FEATURE:
<223> OTHER INFORMATION: target sequence

<400> SEQUENCE: 12

Cys Cys Gly Cys Cys
1               5
```